United States Patent
Johnson et al.

(10) Patent No.: US 9,605,238 B2
(45) Date of Patent: Mar. 28, 2017

(54) PHOTO-BIOREACTOR SYSTEM AND METHOD FOR PRODUCTION OF BIO-MATERIALS

(71) Applicant: Arizona Technology Innovation Group, Inc, Phoenix, AZ (US)

(72) Inventors: Wayne L. Johnson, Phoenix, AZ (US); Steven T. Fink, Mesa, AZ (US); Roxanne E. Abul-Hal, Mesa, AZ (US); N. Alan Abul-Haj, Mesa, AZ (US)

(73) Assignee: Arizona Technology Innovation Group, Inc., Phoenix, AZ (US)

( * ) Notice: Subject to any disclaimer, the term of this patent is extended or adjusted under 35 U.S.C. 154(b) by 158 days.

(21) Appl. No.: 14/493,259

(22) Filed: Sep. 22, 2014

(65) Prior Publication Data
US 2016/0083679 A1  Mar. 24, 2016

Related U.S. Application Data

(60) Provisional application No. 61/885,003, filed on Oct. 1, 2013.

(51) Int. Cl.
*C12M 1/00* (2006.01)
*C12M 3/00* (2006.01)

(52) U.S. Cl.
CPC ............ *C12M 21/02* (2013.01); *C12M 21/14* (2013.01); *C12M 23/02* (2013.01); *C12M 23/22* (2013.01);
(Continued)

(58) Field of Classification Search
CPC ...... C12M 21/02; C12M 31/10; C12M 31/02; C12M 31/08; C12M 23/06; C12M 43/06; C12M 31/12; C12M 43/08; A01G 33/00; C12N 1/12; C12N 1/10; C12N 1/20; C12N 13/00; C02F 3/32; C12P 5/023; C12P 7/649; Y02E 50/13; Y02E 50/343
(Continued)

(56) References Cited

U.S. PATENT DOCUMENTS

2009/0291485 A1    11/2009   Shigematsu et al.
2010/0279395 A1    11/2010   Haley, III
(Continued)

OTHER PUBLICATIONS

International Searching Authority, International Search Report and Written Opinion, International Application No. PCT/US2014/057566, Mailed Dec. 31, 2014, 12 pages.

*Primary Examiner* — Michael Hobbs
(74) *Attorney, Agent, or Firm* — Jennings Strouss & Salmon PLC; Michael K. Kelly

(57) ABSTRACT

A photo-bioreactor and method of operating are described. The photo-bioreactor includes a reactor vessel arranged to contain a fluid medium within which bio-material is grown, and at least one light-emitting rod extending into the reactor vessel, wherein the light-emitting rod has an elongate tubular member characterized by a length along a longitudinal axis and a width along an axis normal to the longitudinal axis, and designed with an outer wall that encloses one or more light-emitting devices arranged along the longitudinal axis, the outer wall being transparent to at least part of the light emitted by the one or more light-emitting devices into the reactor vessel. The photo-bioreactor further includes a drive system coupled to the elongate tubular member, and operatively configured to rotate the light-emitting rod about the longitudinal axis within reactor vessel, and circulate the fluid medium through the reactor.

17 Claims, 22 Drawing Sheets

(52) U.S. Cl.
CPC ............ *C12M 23/58* (2013.01); *C12M 29/08* (2013.01); *C12M 31/10* (2013.01); *C12M 31/12* (2013.01); *C12M 39/00* (2013.01); *C12M 41/08* (2013.01)

(58) Field of Classification Search
USPC ...................................................... 435/292.1
See application file for complete search history.

(56) References Cited

U.S. PATENT DOCUMENTS

2012/0270304 A1 10/2012 Johnson et al.
2012/0282677 A1 11/2012 Brod et al.

PHOTO-BIOREACTOR SYSTEM AND METHOD FOR PRODUCTION OF BIO-MATERIALS

CROSS-REFERENCE TO RELATED APPLICATIONS

Pursuant to 37 C.F.R. 1.78(a)(4), this application claims the benefit of and priority to U.S. Provisional Application No. 61/885,003 filed on Oct. 1, 2013, which is expressly incorporated by reference in its entirety.

BACKGROUND OF THE INVENTION

Field of Invention

The invention relates to systems and methods for producing bio-materials, such as pharmaceutical proteins.

Description of Related Art

A photoautotrophic microorganism is an organism that is capable of generating its own sustenance from inorganic substances using light as an energy source. As an example, photosynthetic microscopic algae, hereinafter referred to as algae, is a photoautotroph. Algae are unicellular organisms which produce oxygen by photosynthesis, and may include flagellates, diatoms, and blue-green algae. More than 100,000 species of algae are known, and it is expected that the actual number of species exceeds 2,000,000. This count does not include genetically modified algae species.

As mentioned above, algae use a photosynthetic process similar to that of higher-developed plants, with certain advantages not found in traditional crops, such as rapeseed, wheat, or corn. Algae have a high growth rate, and it is possible to complete an entire harvest in hours. Further, algae are tolerant to varying environmental conditions, for example, algae may be grown in saline waters that are unsuitable for agriculture. Due to this tolerance to environment and climate, algae are responsible for about one-third of the net photosynthetic activity worldwide.

As a result, during the past decade, much focus has been aimed at the production of algae for commercial purposes. This focus is evidenced by the manifestation of many new industries and uses of algal production, including but not limited to the following: (i) use of algae as a source of fatty acids, proteins and other bio-chemicals in the production of nutraceuticals, health food, food additives, vitamins, pharmaceuticals, and natural dyes; (ii) use of algae as an animal feed supplement with nutritional value equivalent to that of soybean meal; (iii) use of algae as a biological control of agricultural pests; (iv), use of algae as soil conditioners and bio-fertilizers in agriculture; (v) use of algae for the production of oxygen and removal of nitrogen, phosphorus, and toxic substances in sewage treatment; (vi) use of algae in the bio-degradation of plastics; (vii) use of algae as a renewable biomass source for the production of a diesel fuel substitute (biodiesel) and other biofuels such as ethanol, methane gas, and hydrogen; and (viii) use of algae to scrub $CO_2$, $NO_x$, $VO_x$ from effluent released during the production of fossil fuel. With so many uses, it would be desirable to mass produce algae in a low-cost, high-yield manner.

One commercial purpose of significant import includes algae production as a renewable biomass source for sustainable biodiesel production. Presently, the renewable biomass source is provided by edible oils, such as soybean oil, palm oil, and rapeseed oil. It is of interest to develop additional types of renewable biomass sources, such as lipids from algae.

As briefly noted above, one factor making algae interesting as a renewable biomass source is that algae may be grown under conditions or in places not suitable to other sources. Accordingly, algae may be grown and used in ways that do not significantly compete with food sources or agriculturally productive land.

An additional factor making algae of interest is the availability of material to convert to biodiesel or other fuel. Some algae have lipid content as much as 50% to 70% of their dry weight. By way of comparison, the lipid content in dry soybeans is approximately 20%. Algal lipids have a similar composition to vegetable oil and are readily adaptable as a renewable biomass source to existing biodiesel manufacturing processes. Further, the remaining algal biomass may be converted to bio-ethanol, converted to biodiesel, converted to methane, burned, or used as food for other organisms.

As an additional interest, algae can be exploited as commercial sources of Omega 3, Omega 6 oils and Astaxanthin as precursors for pharmaceuticals, nutraceuticals and food supplements.

Commercial acceptance of biomass products is dependent on a variety of factors such as, for example, cost to manufacture, cost to operate, reliability, durability, and scalability. Commercial acceptance of biomass products is also dependent on the ability to increase biomass product growth and recovery, while decreasing biomass production cost. Therefore, it may be desirable to have novel approaches for growing and harvesting biomass products including, for example, cell components such as lipids, proteins, vitamins, fatty acids, minerals, carotenoids, pigments, and the like.

Providing faster growth and producing high density cultures is critical to achieving the operational scale necessary for current environmental and industrial needs. Ideally, improving the speed of growth and increasing the density of a culture will require less production space and consequently will lower the cost of associated facilities.

In line with these reasons and others, the cultivation of algae in liquid suspension compared to algae in stagnant pools allows greater access to the nutrient sources necessary for growth, i.e., water, $CO_2$, and minerals, and permits reducing the production space to a cost-effective footprint. Accordingly, considerable activity has been focused on efficiently growing photoautotrophic microorganisms in liquid suspension, and specifically to mass culture unicellular algae.

Algae production yields are currently adversely affected by many factors. Algal yield can be restricted by the limited wavelength range of light energy capable of driving photosynthesis, between about 400-700 nm (nanometers), which is only about half of the total solar energy. Other factors, such as respiration requirements during dark periods, efficiency of absorbing sunlight, and other growth conditions can affect photosynthetic efficiencies in algal bioreactors. The net result is an overall photosynthetic efficiency that has been too low for economical large scale production. Thus, the need exists for a large scale production system that provides the user a cost-effective means of installation, operation and maintenance relative to production yields. It is desirable that such a system also increase photosynthesis to maximize production yield.

In order to produce optimal yields, algae need to have $CO_2$ in large quantities in the basins or bioreactors where they grow. In addition to $CO_2$, the growth rate of algae may benefit from exposure to other nutrients that are common in known plant fertilizers.

Furthermore, algae need effective control of light. To maximize the growth of photosynthetic organisms, light must be available at the right intensity, the right wavelength, the right frequency, and without excessive heat. Excessive light intensity can limit growth by inducing photo-respiration or bleaching the pigments needed for efficient cell growth. In addition, light intensity or light frequency in excess of the culture requirements may result in heat build-up that can limit culture growth. These problems are readily apparent in production systems that rely solely on direct solar light as a driver of photosynthesis, such as in ponds and raceways. Solar light is subject to extreme diurnal and seasonal variability along with local weather conditions. In addition, cultures relying on direct solar light are subject to periodic heating from light intensities and spectra not immediately useable by the culture.

At high growth rates, algae biomass production is limited by three factors, oxygen content, growth byproducts, and light intensity. Dissolved oxygen becomes a hindrance that limits growth and can poison the algae in the media. Removal of dissolved oxygen is most often accomplished by bubbling air through the media to exchange dissolved oxygen existing above equilibrium with the 20% level in found in air.

During algae production cycles, the media becomes filled with growth byproducts. Richmond, et al described how these byproducts limit growth. Byproducts are often removed by bubbling and subsequently removing the bubbles from the process. Algae growth byproducts are varied but contain oils and other chemicals that readily form bubbles. The bubbles are forced through a small aperture then rinsed to destroy the bubble structure and allow more room for the next bubbles while collecting byproducts and removing them from the media.

To grow at high rates, it is important to efficiently illuminate bio-material, such as algae, throughout the fluid medium using high light intensity. However, high light intensity causes changes in the algae usually referred to as photo-inhibition. Photo-inhibition is characterized by several processes. One such process is the growth of carotenoids that shield the chlorophyll from the light and reduce production. The process has evolved to protect algae that usually operate naturally at low light levels ~70 micromoles/m^2/sec (one sun is 2000 micromole/^2/sec). The second process is a shortening of the antenna between generations of algae in response to intense light. To grow in intense light efficiently, two conditions must be met: (1) the algae must be at high concentration (gm/liter); and (2) the algae must be moved quickly between light and dark regions of the media so that on average the algae get the low level light. The time for these bright flashes and periods of dark are important and must occur on millisecond time scales.

As an example, it is desirable to grow *Spirulina* at high rates at high density with high light intensity. The algae are circulated to produce light and dark pulsation of the light irradiation using almost violent bubbling of the densely loaded media. This method is common and appropriate for *Spirulina*, which is one of the most damage resistant cyanobacteria or algae species known. Other algae species would be damaged by the mechanical damage and shear force in the media flow pattern.

Pumping of algae is common in many algae growth systems. The most common method of pumping is via air lift. Air lift pumping is always counter gravity because it is caused by a difference in density. Air lifting is very energy inefficient and limited on the pumping rate by shear forces that occur at several phases of the pumping (reference). Air lift is best for high flow rate at very low head pressure.

Pumping is a means of damaging algae and providing non-viable cells in the media. Viable algae cells have defenses against attack by bacterial and virus, but non viable cells become food for bacterial and virus. One aim of the development is to provide an environment where algae has high growth rate advantages over bacteria and virus. This environment will enable long time between inoculation and increase production efficiency.

Any media requires fundamental parameters to be productive. The media must have correct nutrients for efficient growth of the algae. For example, sufficient carbon, usually in the form of $CO_2$, must be present. The temperature must be optimized for growth rate. Light must be supplied at levels that match the ability of algae to absorb it efficiently and convert it efficiently to algae biomass. High intensity changes the algae sensitivity to light resulting in a mixed optimum light intensity.

The ability to effectively control light for 24 hours per day as well as continuous consumption of $CO_2$ and other nutrients, encourages faster growth of biomass and secondary metabolites.

These factors result in a more efficient use of facilities, enabling a smaller footprint for a given level of production. However, the use of artificial light has a cost that must be minimized for successful industrial application.

The two major obstacles that reduce the uniform delivery of light to a culture are turbidity and bio-filming. Turbidity occurs as a culture approaches a density where some of the organisms shade others from the light. Ensuring delivery of the appropriate amount of light to each organism becomes increasingly difficult as the density of the organisms in a culture increases. Turbidity within a culture results in some organisms receiving less light than they can utilize while other organisms receive non-productive, or even harmful absorption of light. This absorption of excess light wastes energy and contributes to heat build-up.

Bio-filming is an extremely widespread problem that occurs when a microorganism adheres to a surface. Most microorganisms, including species in all three domains, i.e., bacteria, eukaryotes, and archaea, perform processes that result in adhesion to surfaces and to other microorganisms. In industrial applications, biofilms often clog or corrode pipes and surfaces. In photo-bioreactors a biofilm can form over a light-delivery surface, thereby reducing the intensity and changing the spectra of the light transmitted.

SUMMARY OF THE INVENTION

The invention relates to systems and methods for producing bio-materials, such as pharmaceutical proteins.

According to one embodiment, a photo-bioreactor and method of operating are described. The photo-bioreactor includes a reactor vessel arranged to contain a fluid medium within which bio-material is grown, and at least one light-emitting rod extending into the reactor vessel, wherein the light-emitting rod has an elongate tubular member characterized by a length along a longitudinal axis and a width along an axis normal to the longitudinal axis, and designed with an outer wall that encloses one or more light-emitting devices arranged along the longitudinal axis, the outer wall being transparent to at least part of the light emitted by the one or more light-emitting devices into the reactor vessel. The photo-bioreactor further includes a drive system coupled to the elongate tubular member, and operatively configured to rotate the light-emitting rod about the longitudinal axis within reactor vessel, and circulate the fluid medium through the reactor.

DETAILED DESCRIPTION OF SEVERAL EMBODIMENTS

Figure 1A:
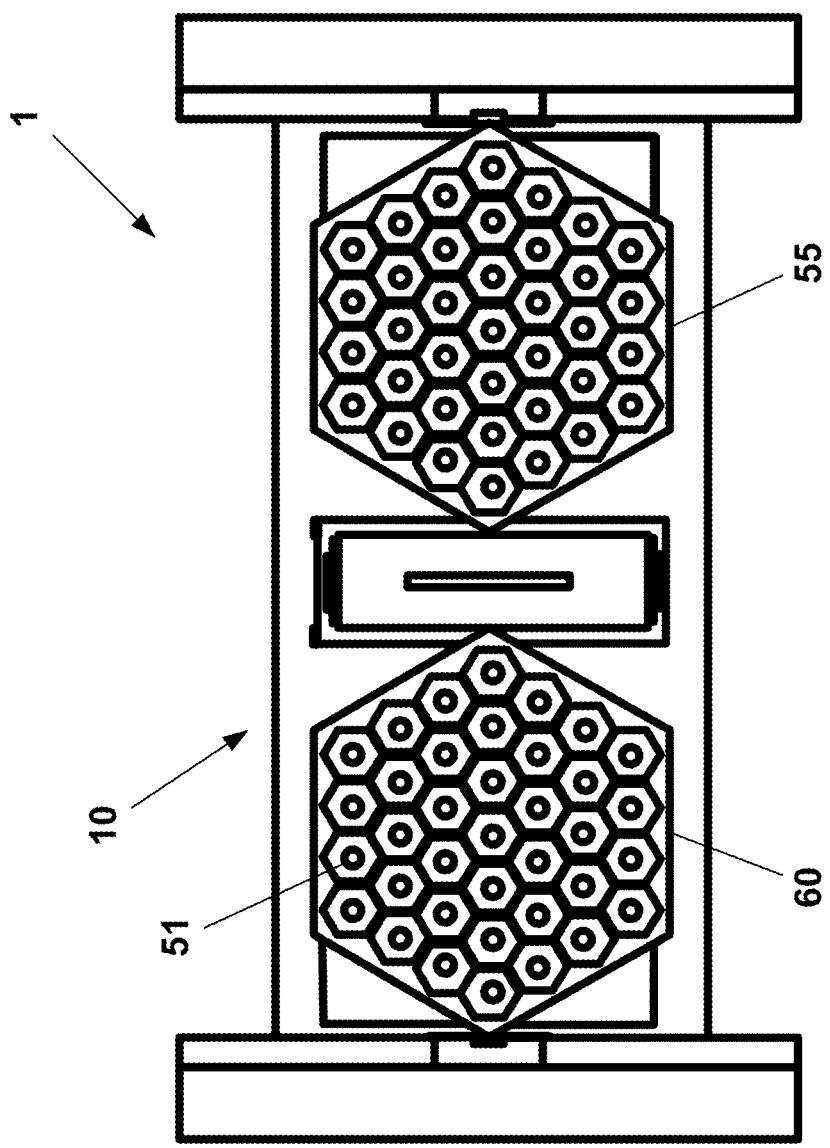
FIG. 1A depicts a top view of a photo-bioreactor according to an embodiment.

A photo-bioreactor and methods of operating are described in various embodiments. One skilled in the relevant art will recognize that the various embodiments may be practiced without one or more of the specific details, or with other replacement and/or additional methods, materials, or components. In other instances, well-known structures, materials, or operations are not shown or described in detail to avoid obscuring aspects of various embodiments of the invention. Similarly, for purposes of explanation, specific numbers, materials, and configurations are set forth in order to provide a thorough understanding of the invention. Nevertheless, the invention may be practiced without specific details. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments. Various additional layers and/or structures may be included and/or described features may be omitted in other embodiments.

The photo-bioreactor and methods of operating includes embodiments that, among other things, address a lower volume and higher value application to production of pharmaceuticals. Pharmaceutical production is applicable to at least 150 FDA approved drugs that are produced by genetically modifying bacteria, often $E.\ coli$. One particular pharmaceutical is insulin. The advantage of the process of generating complex molecules by organic means is that the product is chiral pure. Chiral impurities produce spurious effect in pharmaceuticals that are often detrimental and sometimes dangerous. Removal of chiral impurities is costly and often dominates the cost of production. And, as more complex molecules, such as recombinant proteins, are to be produced, a more complex host is needed. For example, the algae *Chlamydomonas reinhardtii* is readily capable of being modified to produce several useful proteins.

The drugs demonstrated as feasible range from cancer drugs to vaccines. The commercial quantities range from kilograms to 100's of metric tons.

These proteins are expensive averaging ~$300/gram with some exceeding $100,000/gram. These materials are not available in sufficient quantities to test for use as a drug let alone of a reasonable cost to be considered as a viable material to market as a commercial drug while exploiting existing methods of production. Genetic Modified Organism (GMO) Algae may reduce the cost of these drugs and increase availability.

The efforts so far show that the portion of the algae biomass of large value is less than one percent of total batch quantities processed. The low product rate requires considerable growth area by conventional methods. Covered ponds grow at rate of 30 grams/m^2/day requiring substantial real estate.

The pharmaceutical industry has experience in using heterotrophic growth of bacteria and algae materials. Algae are unique when compared to their predators in producing biomass from nonorganic nutrients. This very high growth rate for algae and low generation of organic material that is potential feed for bacteria and viral species will improve culture viability.

GMO algae are under scrutiny as potential ecological threat. Some researchers contend that modifications should be made that would render the algae incapable of being grown outside without some key that is not available in the environment.

Hence, the capital cost of the photo-bioreactor and method of operating described herein (i.e., Spinning Light Rod Photo-Bioreactor, SLRPBR) is compared to other technologies in Table 1 below. This cost does not cover the cost of electrical power used in the SLRPBR which is ~$1,000/kg of drug.

TABLE 1

Comparable cost to produce algae

| Growth Technology | Floor space growth rate (g/m^2/day) | Floor space area to produce 100 kg of drug/yr | Cost/m^2 | Capital cost/ 100 kg of drug/year* |
|---|---|---|---|---|
| Covered ponds | 30 | 3044 | $347 | $1,055,556 |
| PhotoBioReactor | 51 | 1791 | $763 | $1,366,013 |
| SLRPBR | 240000 | 0.38 | $1,070,706 | $407,422 |

*Capital cost includes only the equipment needed to grow algae in a temperature controlled environment excluding inoculation, laboratory support, special equipment for sequestration. Assume 0.003 drug concentration in algae. Predicted power cost ($0.12/kwh) or $3.14/kg algae or ~$1,000/kg of drug for the SLRPBR.

A smaller reactor footprint enabling large comparable surface area of a pond to be enclosed in a factory reduces the cost to sequester the algae species and to protect the algae being grown. A clean environment can be significantly less expensive. And, a rudimentary clean room (class 100) alone can cost ~$5000/m^2, and an additional $250/m^2/month power and maintenance cost.

Systems of this nature are readily automated. For example, it is difficult to automate a pond. Most operations are handled through computer with no manual intervention. The only portions needing manual effort are maintenance which is the inventor(s) goal to reduce through engineering to <10 man hours/month for a production system.

Steam sterilization is reliable, produces little chemical and organic waste, and addresses a broad spectrum of the species that are effectively eliminated. Steam sterilizing is fast requiring <2 hours for an optimally designed system. Steam sterilization works through deposits where the target live organism is encased in a cocoon of material. Steam sterilization requires expense and material and system engineering to operate without equipment derogation.

As described above, high growth rate and elevated production of high density cultures are critical to achieving the operational scale necessary for current environmental and industrial needs. The inventors believe that improving the speed of growth and increasing the density of a culture will require less production space, and consequently, will lower the cost of associated facilities. Therefore, a photo-bioreactor system and method is described below. In particular, a spinning light rod photo-bioreactor (SLRPBR) design is described that can meet at least one or more of the following conditions: high growth rate, high density cultures, sterile environment, system compactness, among others.

Figure 1B:
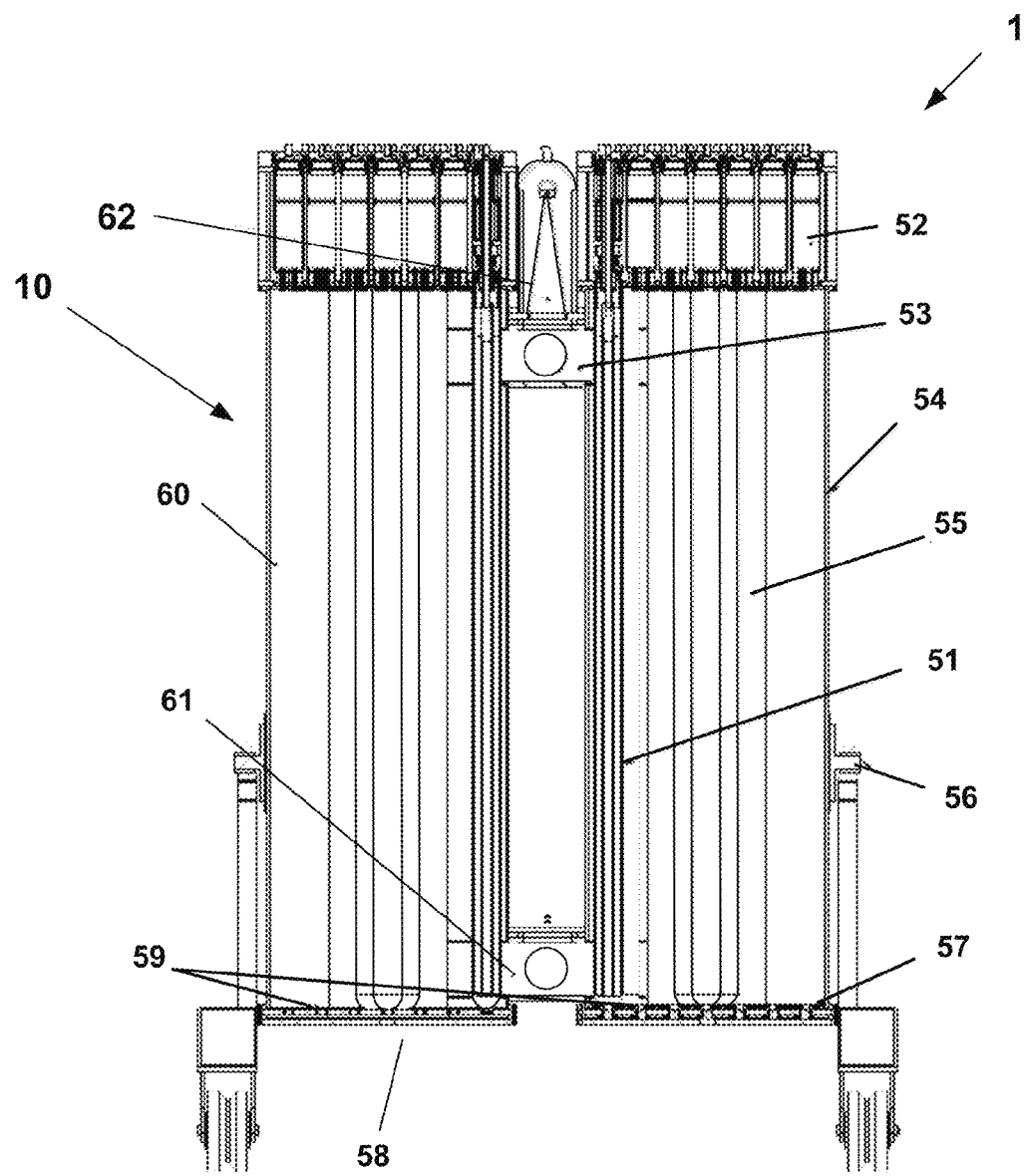
FIG. 1B depicts a cross-sectional, side view of the photo-bioreactor of FIG. 1A.
Figure 1C:
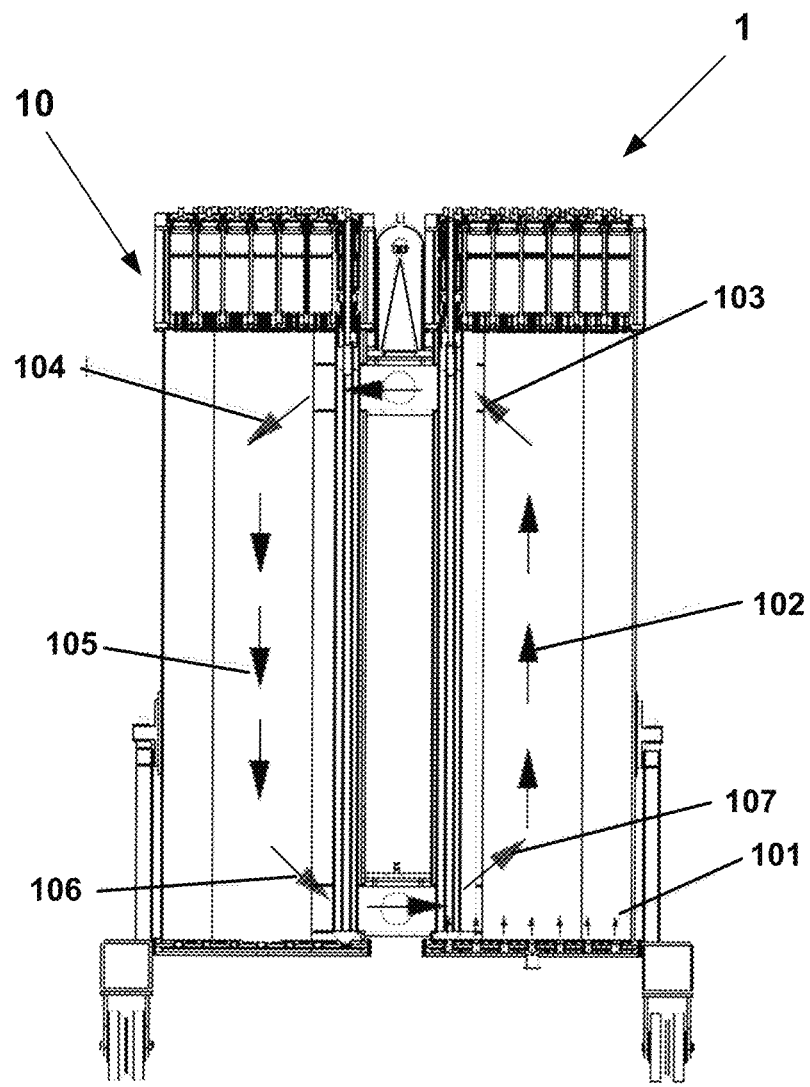
FIG. 1C depicts another side view of the photo-bioreactor of FIG. 1A illustrating the circulation of the fluid medium.

According to one embodiment and as shown in FIGS. 1A through 1C, a photo-bioreactor 1 and method of operating are described. The photo-bioreactor 1 includes a reactor vessel 10 arranged to contain a fluid medium within which bio-material is grown, and at least one light-emitting rod 51 extending into the reactor vessel 10, wherein the light-emitting rod 51 has an elongate tubular member characterized by a length along a longitudinal axis and a width along an axis normal to the longitudinal axis, and designed with an outer wall that encloses one or more light-emitting devices arranged along the longitudinal axis, the outer wall being transparent to at least part of the light emitted by the one or more light-emitting devices into the reactor vessel 10. The photo-bioreactor 1 further includes a drive system 52 coupled to the elongate tubular member, and operatively configured to rotate the light-emitting rod 51 about the longitudinal axis within reactor vessel 10, and circulate the fluid medium through the reactor 1.

FIG. 1A depicts the tanks in elevation and plan view. And, FIG. 1B depicts the tanks in cross-section. The tanks, including up-flow tank 55 and down-flow tank 60, are defined by tank walls 54 and may be hexagonal in cross section (as observed from the top view in FIG. 1A) to minimize dead spaces in the corners. However, the tanks, including up-flow tank 55 and down-flow tank 60, may be of other cross-sectional shape, e.g., circular, square, rectangular, triangular, etc. The tank configuration has a large cross sectional area when viewed normal to the up-flow tank 55 or down-flow 60 vertical axis. Much of that area is filled with an array of light-emitting rods 51 (at least one spinning light rod is shown). The area between the light-emitting rods 51 defines regions of the media cross sectional flow area. Between the vertical tanks are crossover ducts, upper crossover duct 53 and lower crossover duct 61, which are designed to be approximately equal in area to the media cross sectional area. This design assures that the algae moves at uniform flow rate minimizing flow-induced shear stress. While this design condition may be preferred, it is not necessary. Other designs are contemplated.

The upper crossover 53 is fitted with a bubble extractor 62 which is described in greater detail below.

The light-emitting rods 51 may include a spinning head or drive system 52 and the transparent tube with included light source. The bottom of each light rod includes a bearing stub 59 that is fitted into a bearing in an aeration plate 57 in the up-flow tank 55 and the bearing plate 58 in the down-flow tank 60. Trunions 56 allow rotation of the reactor vessel 10 to lay down the assembly.

FIGS. 1B and 1C describe the media flow in the tank configuration. In the bottom of up-flow tank 55 is a gas emitter that generates and air flow (bubbles) 101 through the aeration plate 57. This emitter is used during operation to emit gas (preferably air) that bubble through the algae and lifts it causing flow into lower cross-over duct 106 and flow out of lower crossover duct 107. The lifting causes a counter clockwise flow loop, made of up-flow sections: (1) media lifted by bubbles 102 in up-flow tank 55; (2) flow into upper crossover duct 103 and flow out of upper crossover duct 104; (3) flow downward 105 in down-flow tank 60; and (4) flow into lower crossover 106 and flow out of crossover 107. This aeration causes three functions, among others: (1) it extracts dissolved oxygen from the algae; (2) it mixes the algae between the tank areas; and (3) it removes algae growth products from the media.

Figures 2A, 2B, 2C:
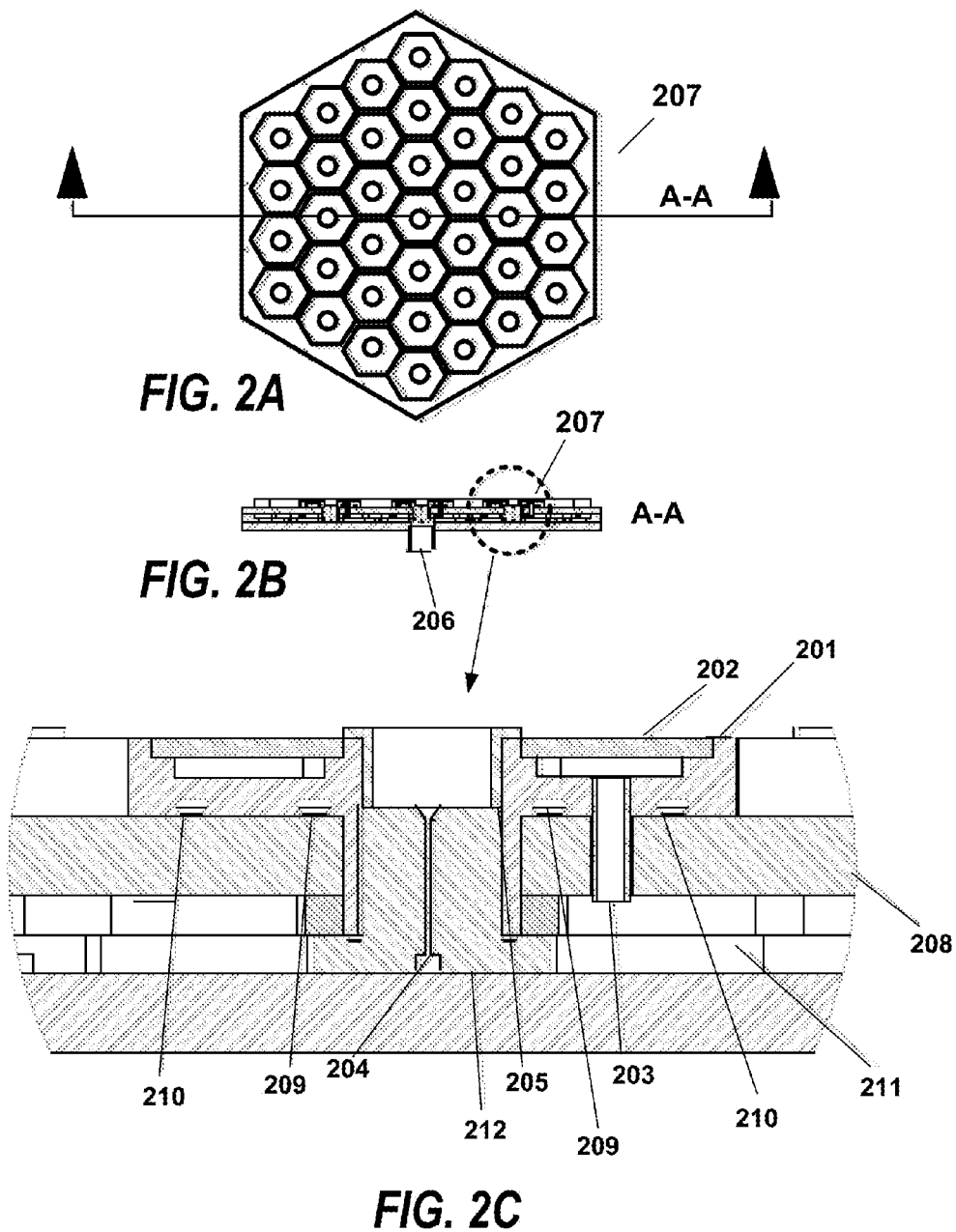
FIGS. 2A through 2C depict both a top view and a cross-sectional view of an aeration plate for use in the photo-bioreactor of FIGS. 1A-C.

FIGS. 2A-2C show an aeration plate 207 according to an embodiment. FIG. 2A provides a top view, FIG. 2B provides a cross-sectional view, and FIG. 2C provides an exploded, cross-sectional view. In this depiction, the aeration plate 207 is comprised of an array of aeration emitters. Each emitter (preferred design) is comprised of a sintered, stainless steel aeration powdered metal membrane 202 welded into machined stainless steel aeration membrane housing 201. These stainless steel aeration membrane housings 201 are mounted and sealed with O-ring 209 and O-ring 210 into a bottom plate 208, below which is a plenum 211 for distribution of gas uniformly over the area of the tank. The plenum 211 is connected to the area behind the powered metal membrane 202 with a tube 203.

At the center of each aeration emitter on the tank facing side, a bearing 205 is located into which is fitted the end of the light-emitting rod. Each bearing is bottomed in a removable bearing plug 212. This bearing plug 212 is designed with a metering passage 204 to control a low flow by each bearing. This flow minimizes media intrusion onto the bearing area and damage to algae in the media.

The bottom plenum 211 is connected to gas supply by a fitting 206 (see FIG. 2B), which is plumbed to valves enabling switching between air for growth operations and steam for cleaning operations. For example, plumbing similar to that used in dairy operation will enable a clean, economical, and maintainable system.

Figure 3:
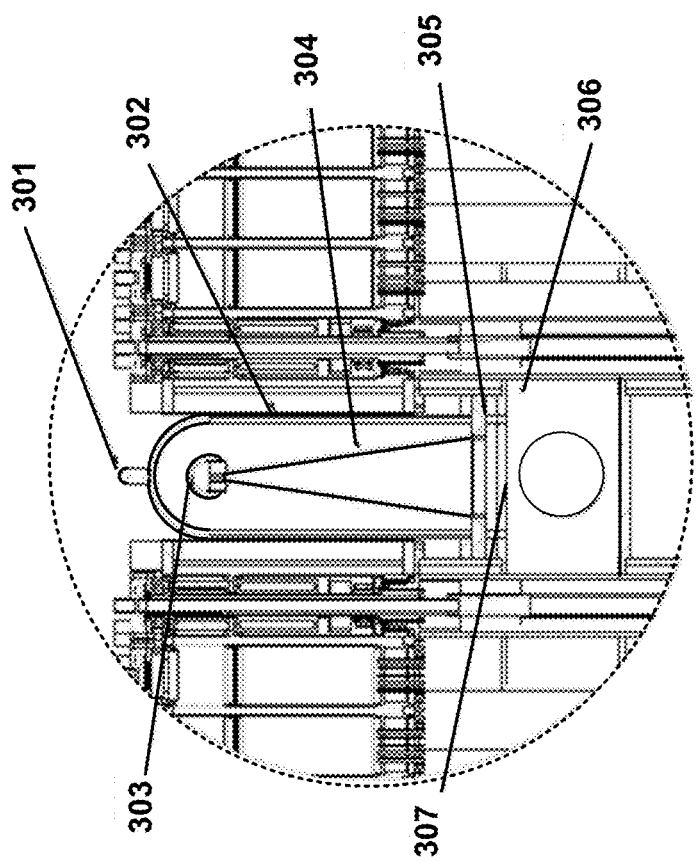
FIG. 3 depicts a cross-sectional view of a bubbler assembly for use in the photo-bioreactor of FIGS. 1A-C.

FIG. 3 shows a close up view of the upper crossover duct 306, which was depicted in FIGS. 1B and 1C, according to an embodiment. This upper crossover duct 306 has a system that releases the air flow injected by the aeration plate used to remove dissolved oxygen and provides the lift energy to pump the media around the tank flow loop.

The close up view shows a nozzle configuration, bubbler flue 304 that extrudes the bubbles that enter the opening 307, that are formed by air moving through the media. These bubbles have a high concentration of algae growth byproducts. The bubbles are extracted through an opening and around a spray protection rain hat 303. From the top of bubbler housing 302, a spray from a spray bar 301 rinses the bubbles into solution and down the outside of the bubble flue 304 and into a collection trough 305. The collection trough 305 is connected to an outside plumbing fitting that drains the system into a container for disposal or extraction for other applications.

Figure 4:
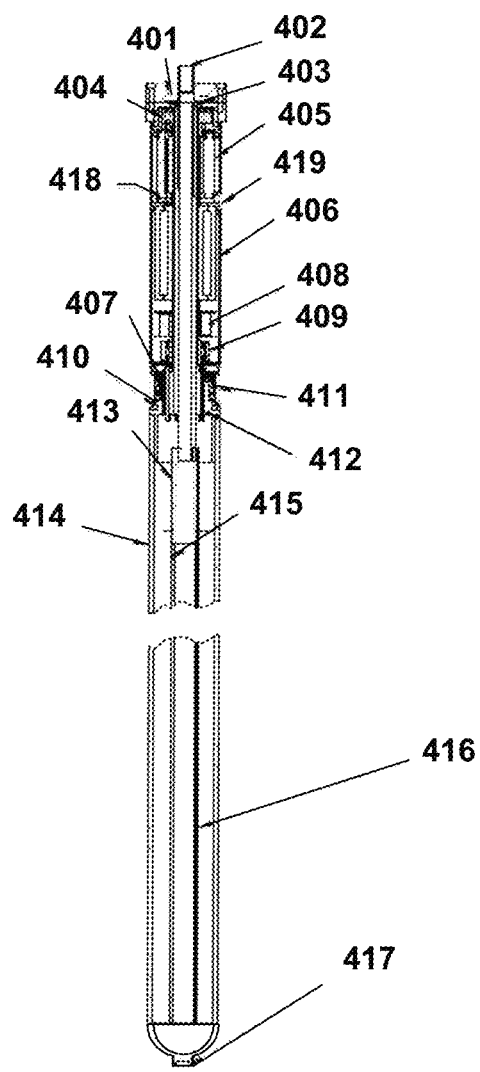
FIG. 4 depicts a light-emitting rod according to an embodiment.

FIG. 4 shows the assembly of the rotation head and light-emitting rod, including spinning light glass tube 414, according to an embodiment. This figure is a cross sectional view cut in the vertical plane. The upper portion of this figure is the rotation head which rotates the spinning light glass tube 414 and provides power to the LEDs in spinning light glass tube and bidirectional data transfer to the rotating parts of the assembly.

The rotating part of the system includes the rotor of motor 405, the rotor shaft 418 which contains the power and data feed-thru 412, inner parts of upper bearing 404, and lower bearings 411, inner part of split core ferrite transformer 406, circuit protection fuses 409, rotating part of RF (radio frequency) data PCB (printed circuit board) pair 407, and cooling block, and bridge rectifier 408.

The stationary part of the rotating head includes outer parts of the stator of motor 405, upper bearing 404, lower bearing 411, fluid seal 403, chamber seal 410, the outer part of the split core ferrite transformer 406, the stationary PCB pair 407 that provides RF communications of the data from the rotation environment to the stationary environment, and the rotation assembly housing 419. This housing mounts in a flange (not shown) and together they comprise the upper enclosure of each tank.

The lower part of the spinning light rod assembly includes spinning glass tube 414 and a hex finned tube 416 upon which the LEDs 415 are fitted. Between the hex finned tube 416 and the rotor is a transition section that supports the power conditioning circuits 413 for the LEDs 415. Glass bearing stub 417, as well as thermal fluid output channel 401 and thermal fluid input 402 are also shown.

LEDs 415 may include organic light-emitting diodes, and may come in a variety of forms, including standard high intensity, super bright, low current types, and the like. The "color" or peak emission wavelength spectrum of the emitted light generally depends on the composition and/or condition of the semi-conducting material used, and may include peak emission wavelengths in the infrared, visible, near-ultraviolet, and ultraviolet spectrum. Typically, the LED's color is determined by the peak wavelength of the light emitted. For example, red LEDs have a peak emission ranging from about 625 nm to about 660 nm. Examples of LEDs include bi-color, tri-color, and the like. Emission wavelength may also depend on the current delivered to the LEDs.

Certain biomasses, for example, plants, algae, and the like comprise two types of chlorophyll, chlorophyll A and chlorophyll B. Each type possesses a characteristic absorption spectrum. In some case, the spectrum of photosynthesis of certain biomasses is associated with, but not identical to, the absorption spectra of, for example, chlorophyll. As an example, the absorption spectra of chlorophyll A may include absorption maxima at about 430 nm and 662 nm, and the absorption spectra of chlorophyll B may include absorption maxima at 453 nm and 642 nm. In some embodiments, the LEDs may be configured to provide one or more peak emissions associated with the absorption spectra of chlorophyll A and chlorophyll B. A combination of LEDs of custom design can be crafted to match the adsorption spectra exactly.

Figure 5:
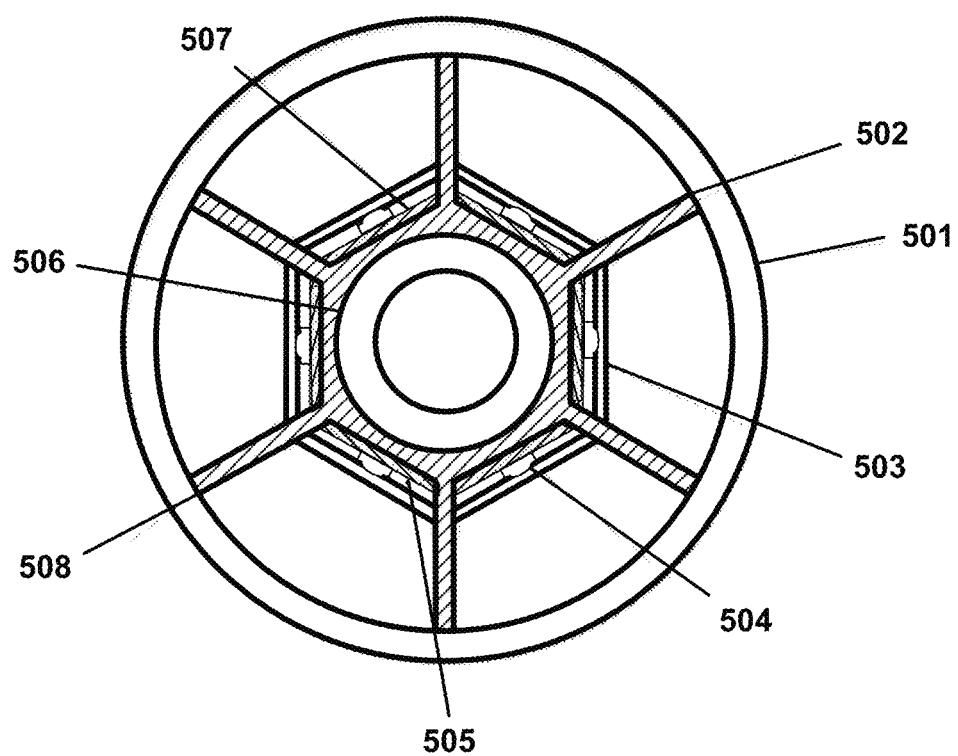
FIG. 5 depicts a cross-sectional view of the light-emitting rod of FIG. 4.

FIG. 5 shows a cross section of the lower part of the spinning light rod assembly according to an embodiment. The LEDs 504 are protected from optical deterioration by the thermal control fluid by a glass cover plate 503. The glass is affixed to the printed circuit board (PCB) 505 with optical epoxy 507. The PCB 505 is comprised of metal plate with thin and very conductive dielectric layers. These boards are very thermally conductive and remove waste heat from the LEDs 504. The PCB 505 is attached to the flats adjacent and between fins 508 on the finned hex extrusion 502 with thermal grease or epoxy. These LEDs 504 are designed to produce more that 10 times the light intensity that saturates the growth rate at low flow rates. The movement of algae moves so that the time average light power per algae cell is no more than in an optimized low flow environment. The LEDs 504 are arranged on the PCB 505 in a pattern that provides uniform light on the outside of the glass tube 501.

Temperature control fluid is pumped down the center tube, facilitating center tube flow 506 and provides temperature control to the first the electronics on the top of the light bars and then to the LEDs 504 themselves. Finally, the fluid thermally controls the temperature of the algae growth media. This system is easily capable of controlling media temperature +/−2.5 degrees C.

Figure 6:
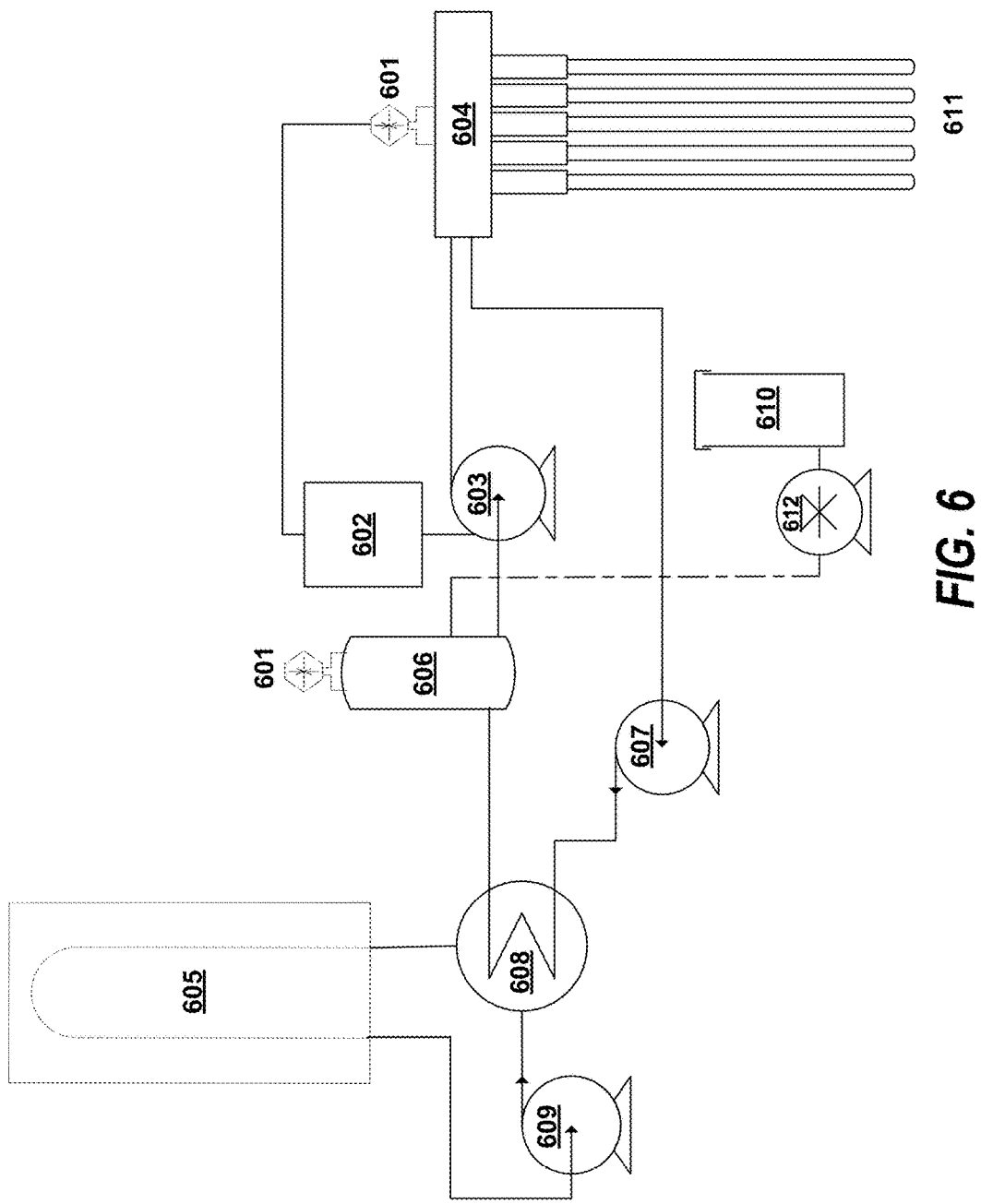
FIG. 6 illustrates a photo-bioreactor system according to an embodiment.

FIG. 6 shows a schematic of the photo-bioreactor, including a thermal control system, according to an embodiment. The temperature control fluid is injected into at least one of the light rods of the photo-bioreactor 611, i.e., the spinning light rod reactor. Upon exit from each light rod the fluid is collected in manifold plate 604, and pumped through coolant pump 607 and coolant-chiller fluid heat exchanger 608, through surge tank 606 and coolant pump 603 and back to the manifold 604 and into the array of light rods. The pressure on the manifold 604 is measured by sensor array 601, and the sensor signal is used to control pressure on the manifold 604, and by extension, the glass portion of the light rods. The system is charged in the coolant surge tank 606 at a system pressure derived by sensor array 601, and supplied by coolant feed pump 612, that is connected to coolant storage 610, to a pressure to prevent cavitation at the inlet of the flow pump. A second flow loop moves fluid by pressure supplied by chiller fluid pump 609 through the other side of coolant-chiller fluid heat exchanger 608 and through chiller 605 where the heat is rejected to the environment or coolant stream.

Figure 7:
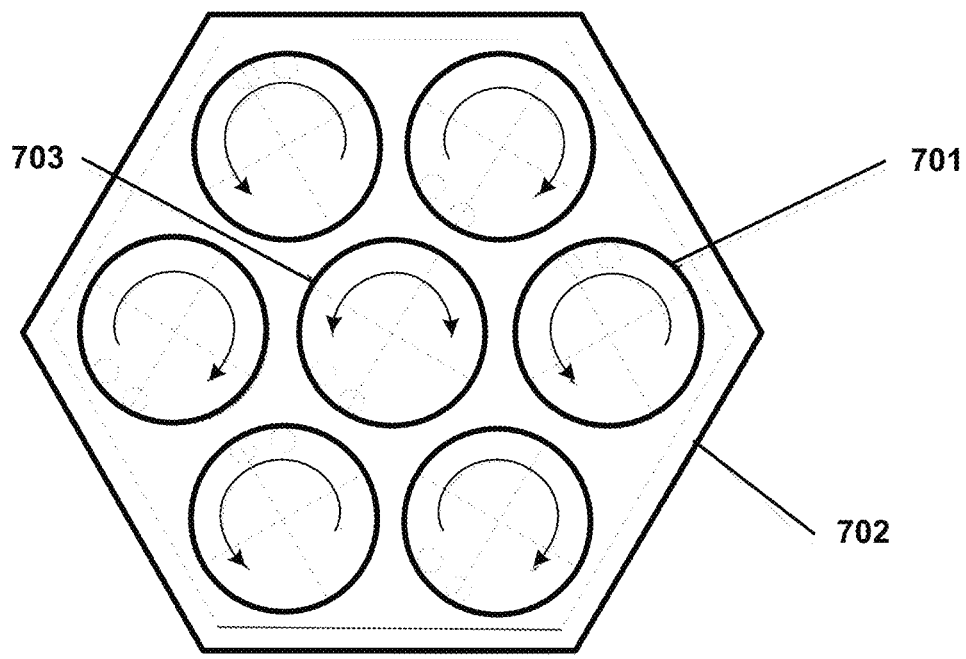
FIG. 7 illustrates a hexagonal pattern of light-emitting rods according to an embodiment.

FIG. 7 shows the geometry of a basic cell 702 of spinning light rods (i.e., light-emitting rods) according to an embodiment. This configuration identifies an array of rods (e.g., 7), including a center spinning light rod 703, surrounded by a number (e.g., 6) of other spinning light rods 701 in plan view (looking from the top). These rods are spun at speeds up to several thousand RPM (revolutions per minute) and limited by the speed at which shear forces cause algae damage. Spinning direction is indicated by arrows indicated on each spinning rod. Estimates are that the dark times are <3-7 ms (milliseconds) and light times of <1-3 ms.

Figure 8:
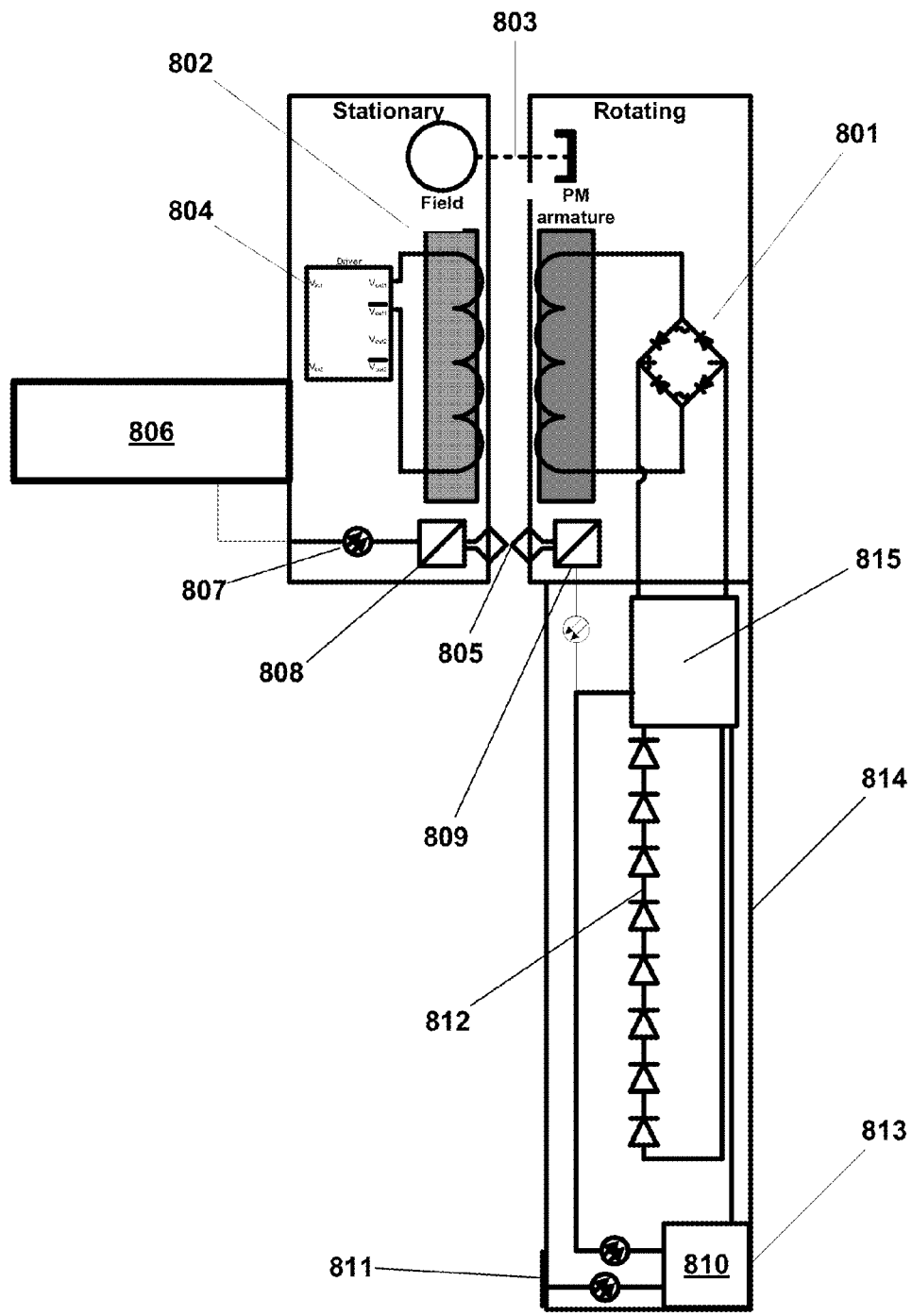
FIG. 8 schematically illustrates a light-emitting system for a photo-bioreactor according to an embodiment.

FIG. 8 shows a schematic of the power and control system for the LED series strings/arrays 812 housed within elongate tubular member 814, and frameless brushless motor 803 according to an embodiment. This power supply concept controls the power to the LEDs and records LED operation during the processing operations. A programmable switching power supply 804 generates at high frequency to enhance coupling across the split ferrite core with winding transformer 802. The power is then rectified to DC by bridge rectifier 801. The power is then transferred to the flooded portion of the power control electronics circuit protection 815. The voltage is measured as well as the current in the strings of LED series strings 812. This data is coupled to the bidirectional RF optical data link 805 and then to bidirectional RF optical data link 808 for transfer by fiber optic cable to the control system. This data includes voltage and current of several or each LED string/array, temperature at specific positions of fluid and media, and data form optical measurements using photo chemical reactive surface(s) 811 of media. Each measurement is logged and used to provide closed loop control of the system. As an example, the set point voltage is programmed to provide specified power from the LED series strings/arrays 812. The measured voltage is compared to the set point and the pulse width or frequency of the power supply is adjusted to provide control of the LED series strings 812 light output. Distributed and central control system 806, fiber optic link 807, and optical system to interrogate patch 813 not defined.

Figure 9:
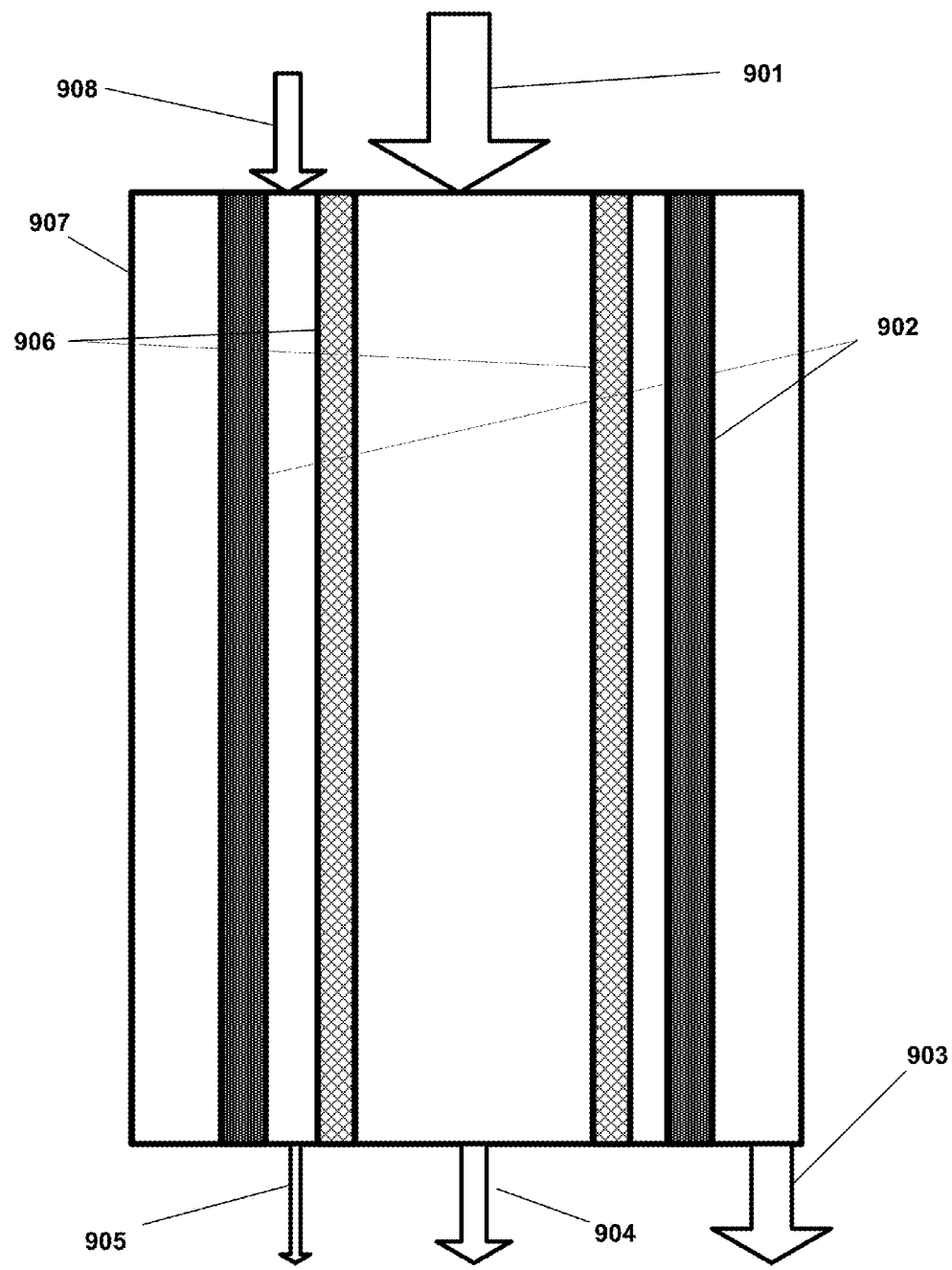
FIG. 9 depicts a harvesting system for a photo-bioreactor according to an embodiment.

FIG. 9 shows a schematic of a system for filtering the media, enclosed in filter vessel 907, according to an embodiment. This method is preferred over bubble extraction of growth byproducts. In this system, a stream of media and algae is identified as input algae and used media 901 as it flows in the interior of tubular fine filter material 906 element. This element has relatively large holes and passes all elements in the media except for the algae itself. The output is a partially dewatered algae stream that is identified as output flow of concentrated algae and some media 904. The level of dewatering depends upon residence time and pressure across the media membrane. One algae target for this *Chlamydomonas reinhardtii* which is about 10 microns in size, which is relatively large for micro-filters. The second coaxial ultra-fine filter material 902 has small pores and passes water and nutrients only. This flow, including water and nutrients 903, is treated and returned to the media. Trapped between the two filters are the growth byproducts. These flow of output of algae growth byproducts 905 are removed from the system for extraction or disposal. Additionally, a push fluid 908 may be added to the space between the filters 902, 906 to dilute the byproduct.

Figure 10:
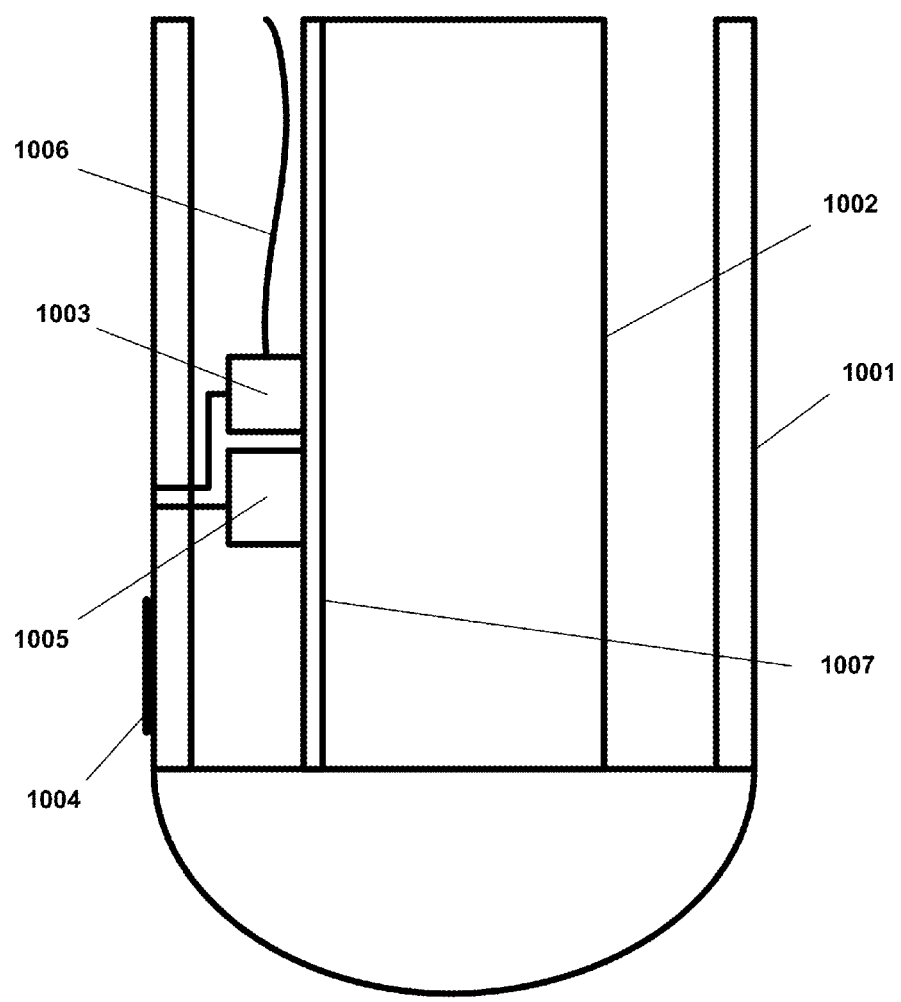
FIG. 10 provides a cross-sectional view of a light-emitting rod according to an embodiment.

FIG. 10 shows a schematic view of a cross section of a light tube according to an embodiment. It is fitted with a special LED and sensor. These items are operated, e.g., pulsed, and circuitry is included that enables measuring the spectral response of material in osmotic contract with the media. These materials can measure pH, dissolved oxygen, nutrients, etc. The target materials are often placed in an adhesive spot. In cross-section, light-emitting rod includes glass tube 1001, core of hex extrusion 1002, PCB board 1007 mounted thereon for power, fiber optic receiver 1003 with fiber optic cable 1006 for data and instruction, LED programmed light source 1005, and sensor 1004.

Figure 11:
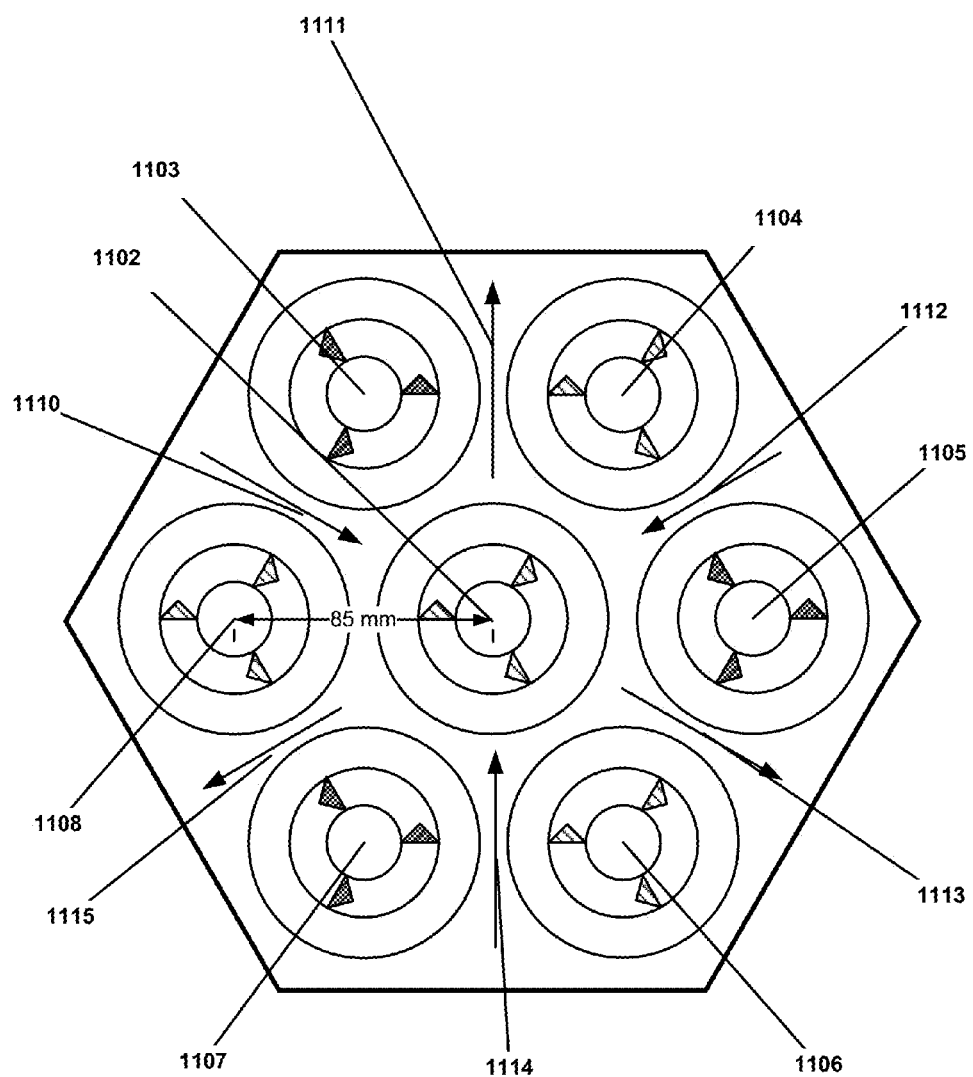
FIG. 11 illustrates a cross-sectional view of the flow pattern in a hexagonal pattern of light-emitting rods according to an embodiment.

According to an embodiment, FIG. 11 illustrates a hexagonal configuration of light-emitting rods (light rods) 1102-1108, wherein flow of fluid medium is directed inward towards light-emitting rod 1102 through in-rod pumping spaces 1110, 1112, and 1114, and flow of fluid medium is directed outward through out-rod pumping spaces 1111, 1113, and 1115. Counter-rotation of adjacent light-emitting rods can generates such a flow pattern, for example.

Figure 12:
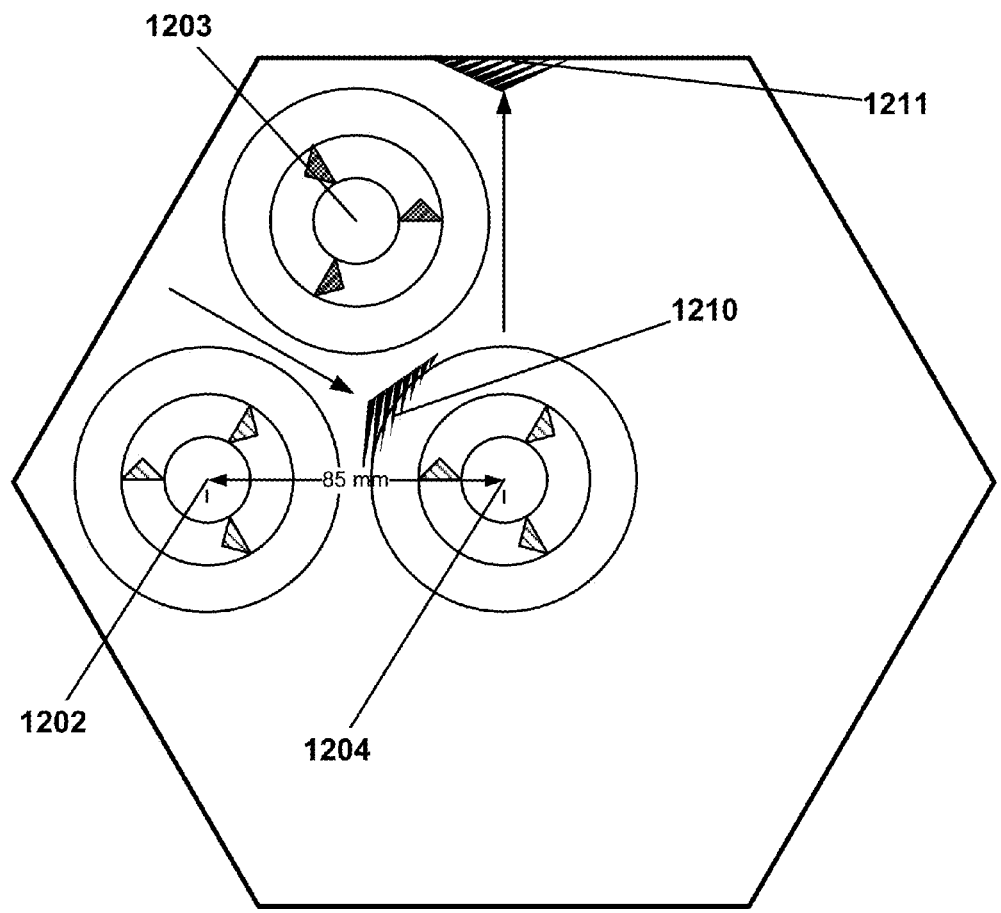
FIG. 12 further illustrates a cross-sectional view of the flow pattern in a hexagonal pattern of light-emitting rods according to an embodiment.
Figure 13:
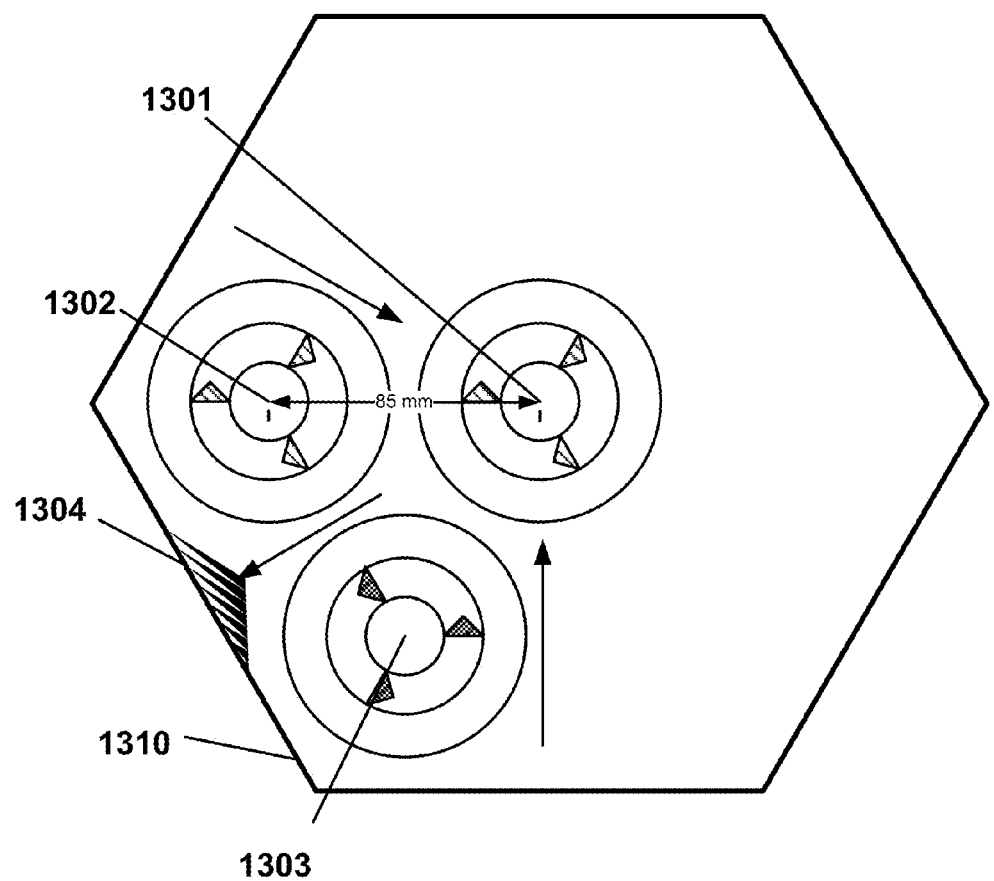
FIG. 13 provides a detailed view of the flow pattern in an array of light-emitting rods according to an embodiment.
Figure 14:
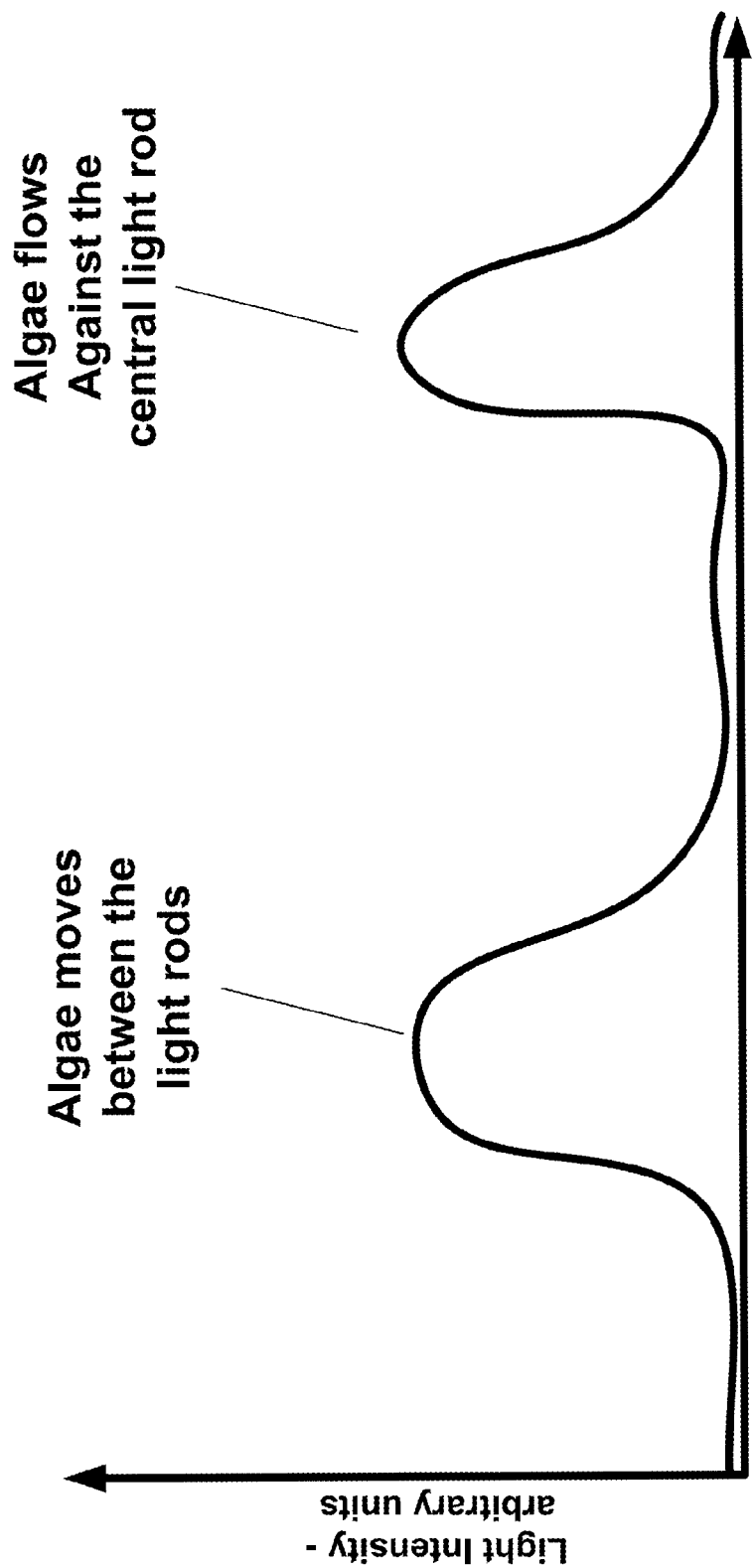
FIG. 14 illustrate an exemplary light intensity cycle to which bio-material is exposed in a photo-bioreactor according to an embodiment.

According to another embodiment, FIG. 12 illustrates a hexagonal configuration of light-emitting rods (light rods) 1202, 1203, and 1204, wherein high shear zones 1210 and 1211 can occur. According to another embodiment, FIG. 13 illustrates a hexagonal configuration of light-emitting rods (light rods) 1301, 1302, and 1303, wherein high shear zone 1304 can occur at container wall 1310. According to another embodiment, FIG. 14 illustrates the light intensity fluid medium (e.g., algae) is exposed to when passing between rods and approaching the center rod. As evident in FIG. 14, the media including algae may be subjected to periods of relatively higher light intensity (e.g., bright periods) and other periods of relatively lower light intensity (e.g., dark periods).

Figure 15:
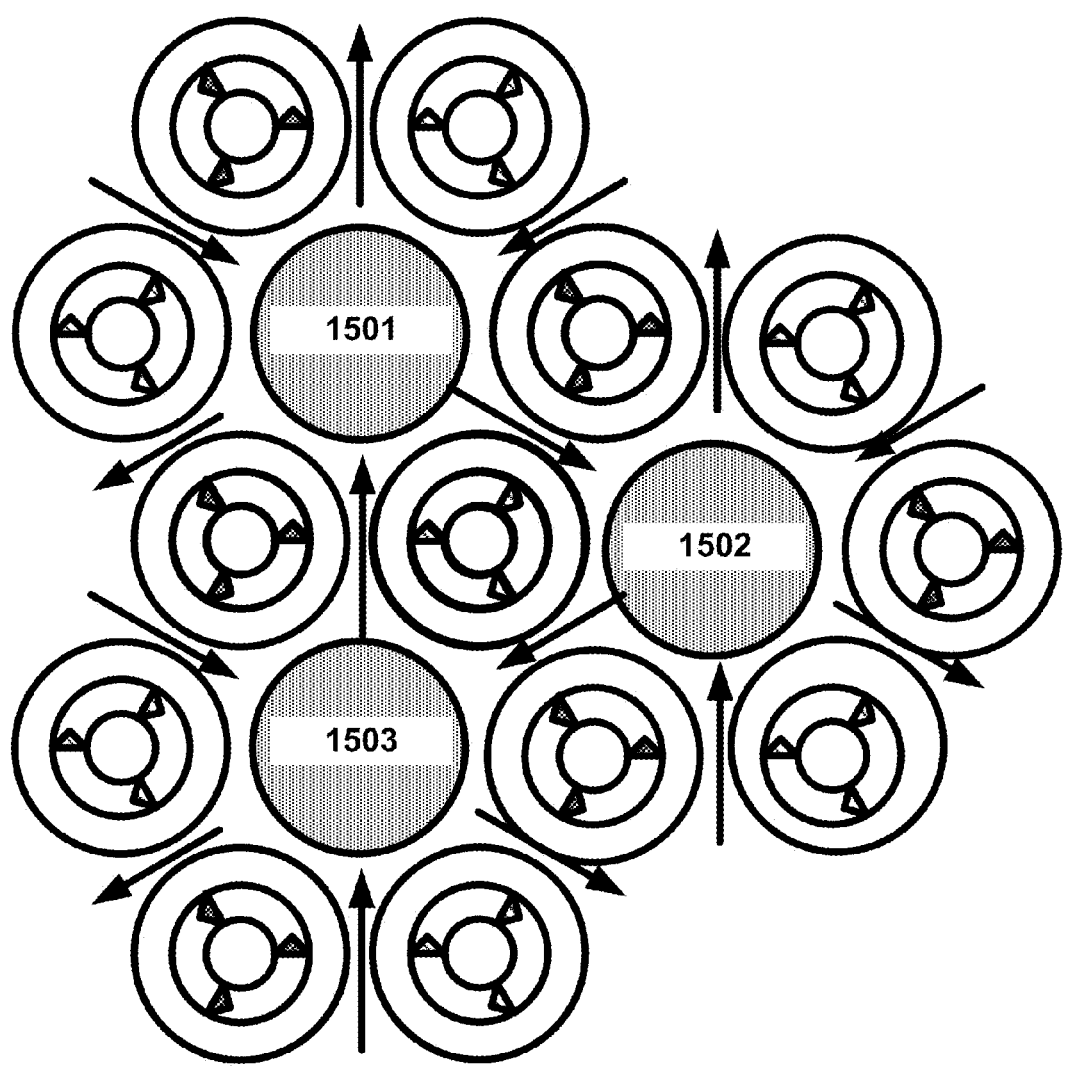
FIG. 15 illustrates a cross-sectional view of the flow pattern in a hexagonal pattern of light-emitting rods according to another embodiment.
Figure 16:
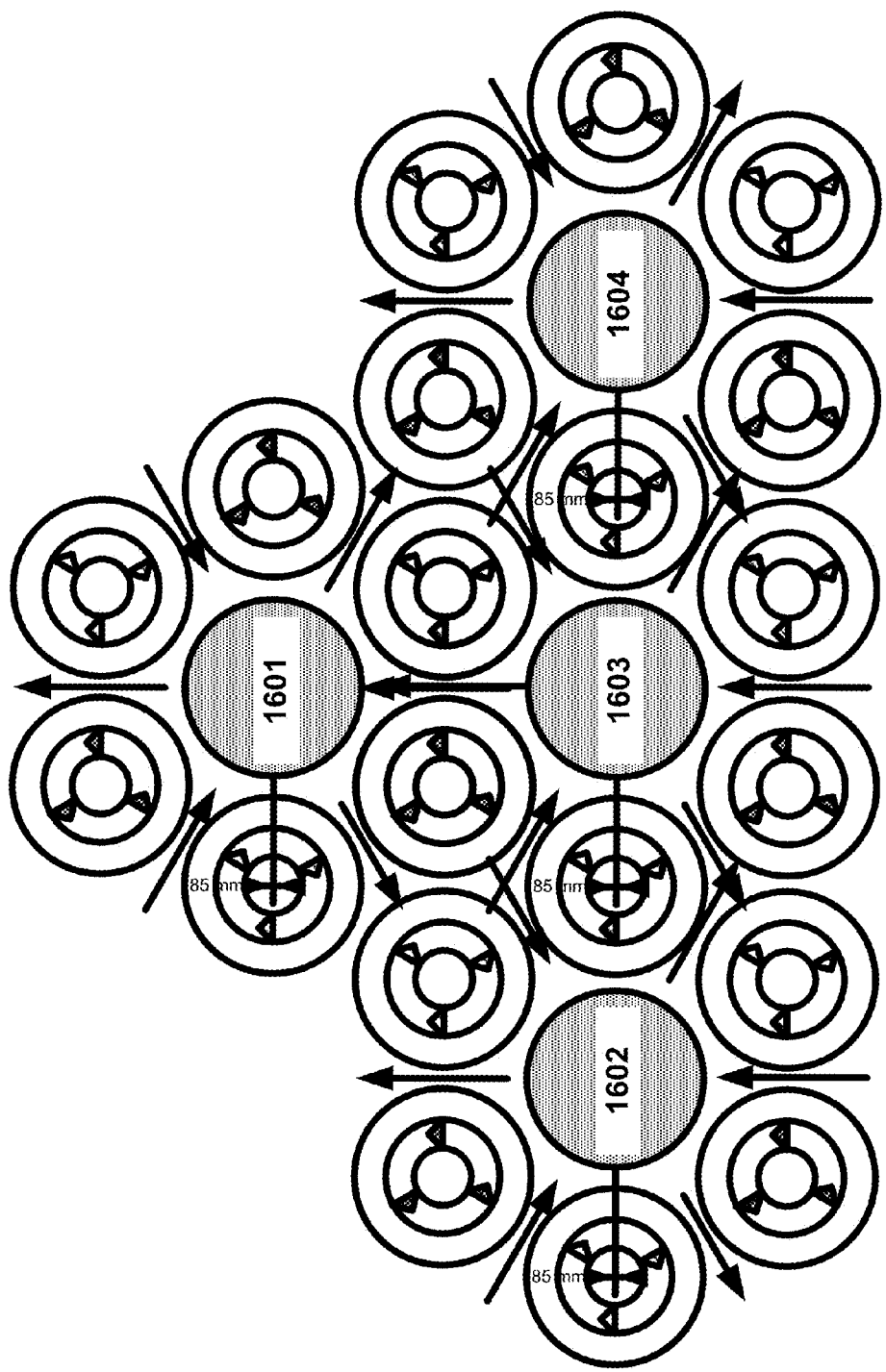
FIG. 16 illustrates a cross-sectional view of the flow pattern in a hexagonal pattern of light-emitting rods according to yet another embodiment.

According to yet another embodiment, FIG. 15 illustrates plural hexagonal light-emitting rod configurations that are integrated, including center light-emitting rods 1501, 1502, and 1503. According to even yet another embodiment, FIG. 16 further illustrates plural hexagonal light-emitting rod configurations that are integrated, including center light-emitting rods 1601, 1602, 1603, and 1604.

Figure 17:
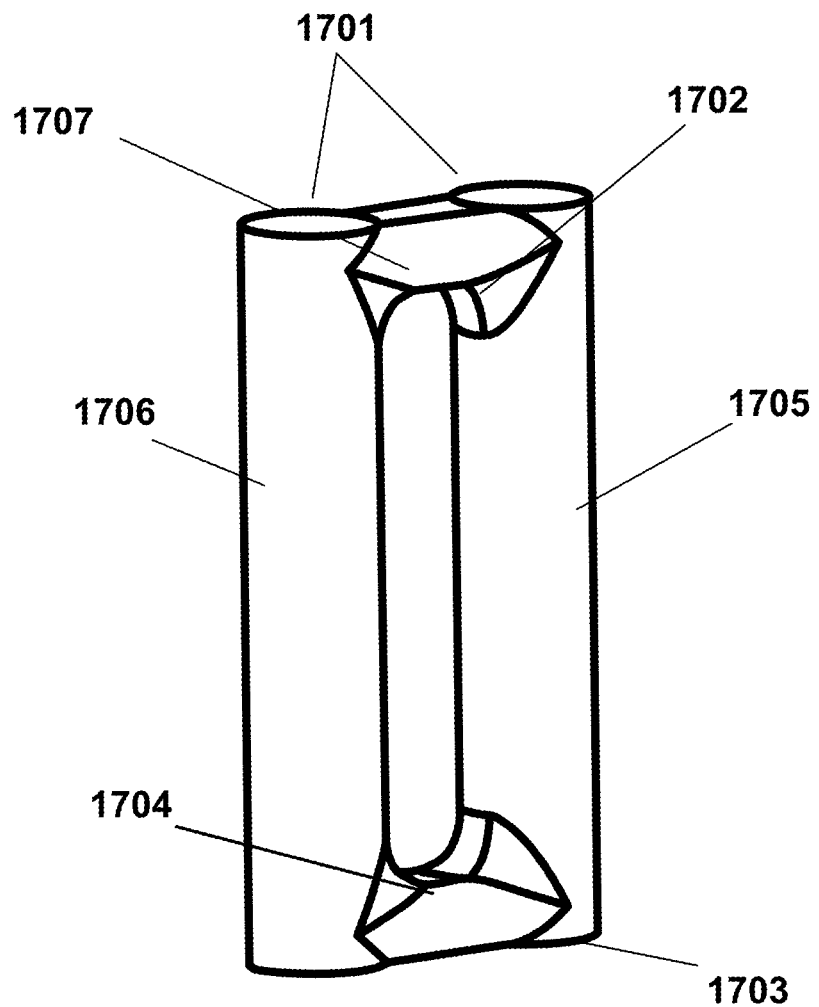
FIG. 17 provides a reactor design according to an embodiment.
Figure 18:
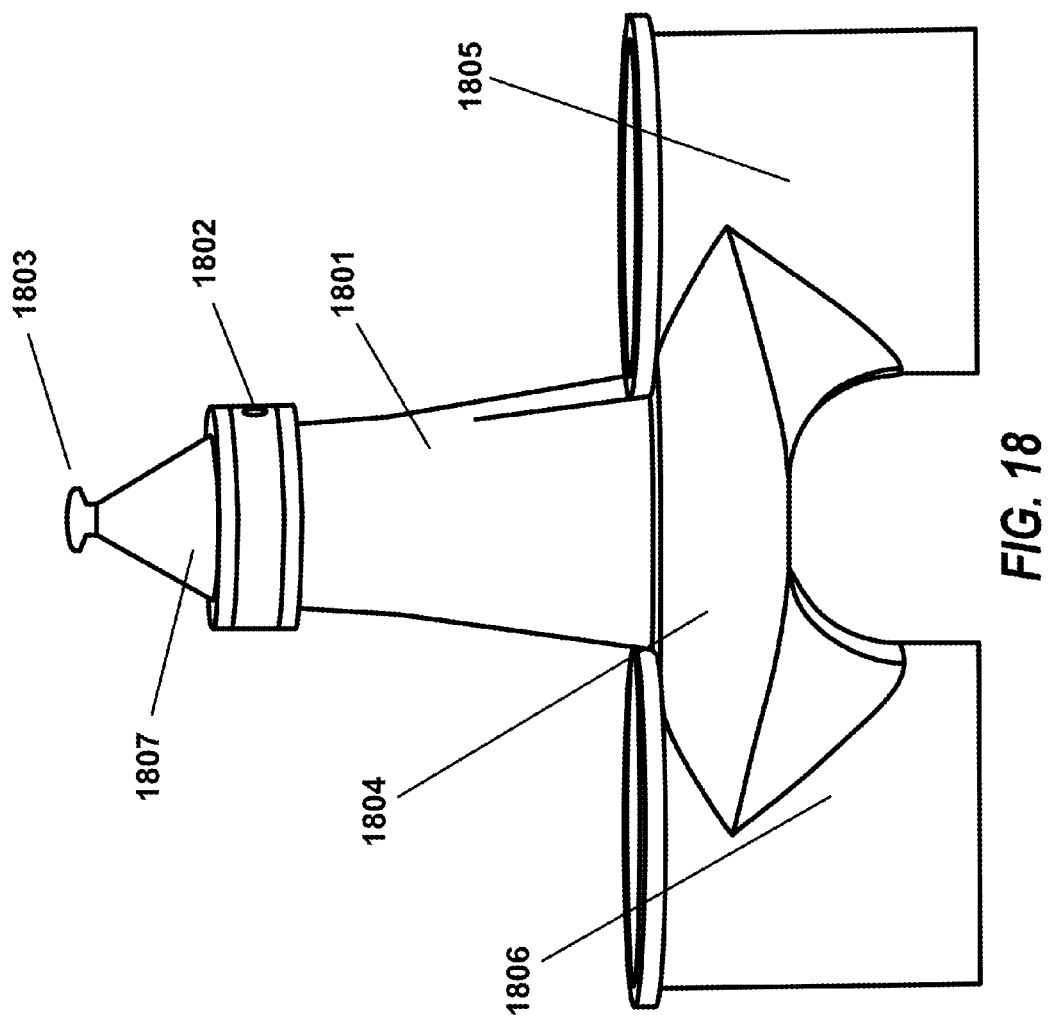
FIG. 18 provides an upper portion of the reactor design depicted in FIG. 17.
Figure 19:
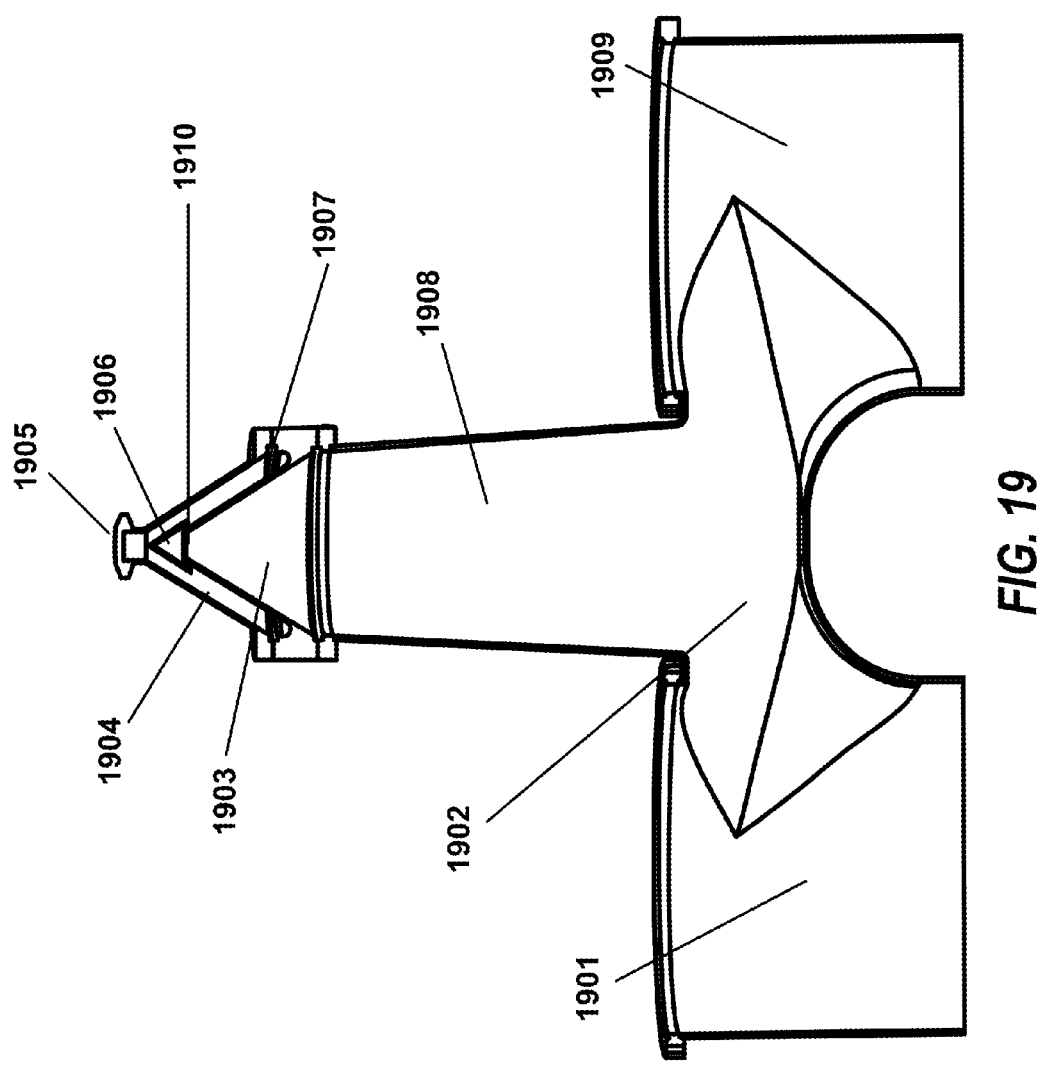
FIG. 19 provides a cross-sectional view of a bubbler system according to an embodiment.
Figure 20:
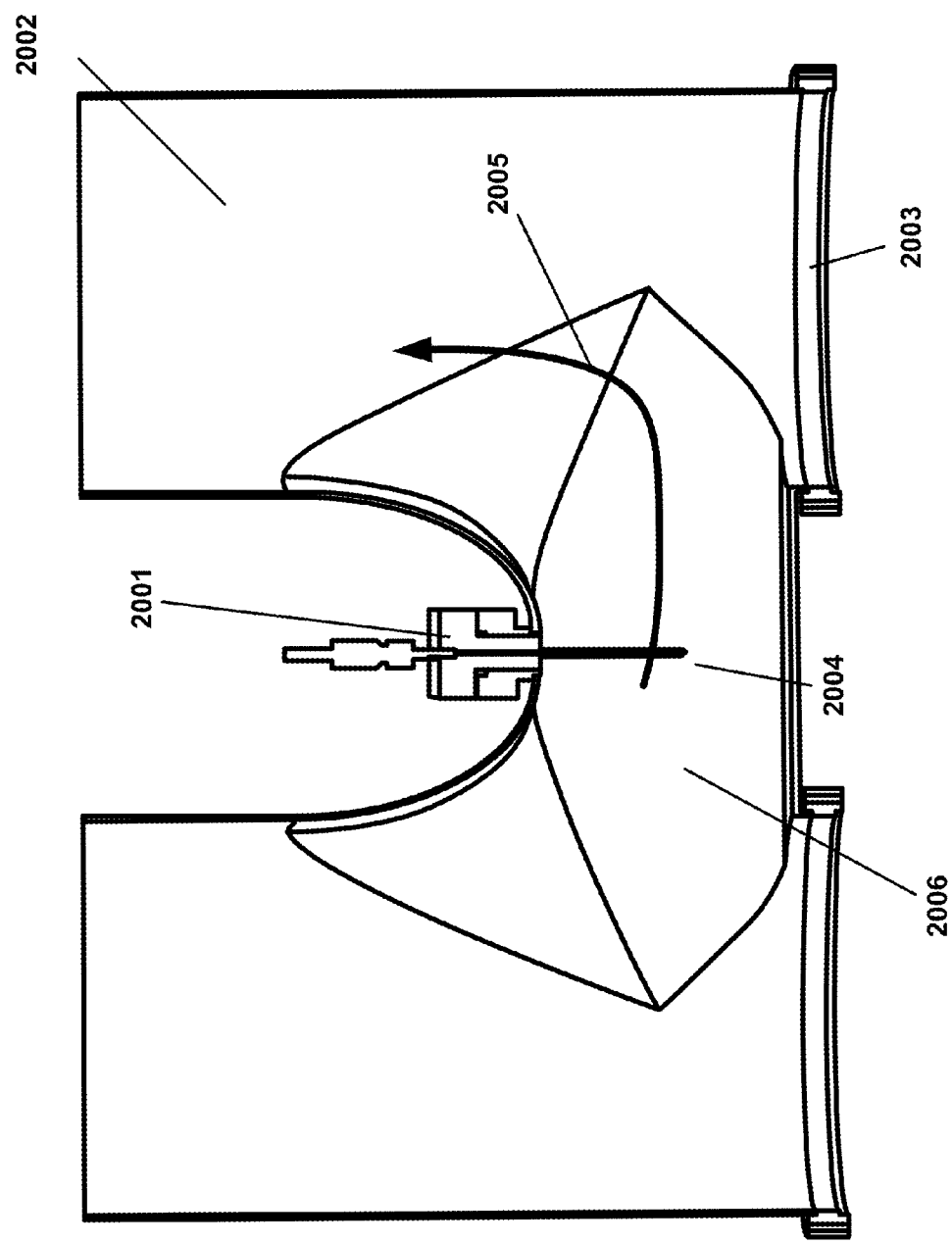
FIG. 20 provides a lower portion of the reactor design depicted in FIG. 17.

FIGS. 17 through 20 illustrate in perspective view a reactor tank according to an embodiment. FIG. 17 depicts up-flow tank 1705, down-flow tank 1706, lower cross-over duct 1704 (with sensor mounting), upper cross-over duct 1707, flanges 1701 to mount light-emitting rods, aeration flange 1703, and smooth saddle flow transition 1702. FIG. 18 depicts up-flow tank 1805, down-flow tank 1806, upper cross-over duct 1804, bubble collector 1801, bubble extractor 1807, drain 1802 for bubble fluids, and spray nozzle 1803. FIG. 19 depicts in cross-section up-flow tank 1909, down-flow tank 1901, upper cross-over duct 1902, bubble collector 1908, bubble extractor inner cone 1903, bubble extractor outer cone 1904, bubble extraction orifice 1910, bubble fluid collection 1907, spray nozzle 1905, and rain cap 1906. FIG. 20 depicts in cross-section up-flow tank 2002, lower cross-over duct 2006, aeration flange 2003, sensor 2004 mounted on sensor flange 2001 for mounting sensor 2004 and measuring fluid medium flow 2005.

According to other embodiments, a photo-bioreactor for growth of bio-material, such as cyanobacteria or algae, is described, wherein: (a) The light is supplied in a transparent tube immersed in the growth media; (b) The tubes are spun to move the algae between the lighted surfaces to create a light-dark pulsation to the light for growing the bio-material; (c) The algae grows at relatively high density with relatively low loss of viable algae through damage by the pumping, wherein care is taken to remove dissolved oxygen and growth byproducts and provide availability of sufficient nutrients. The high density algae has a light absorption depth of approximately 4 mm (millimeters) and densities in excess of about 50 gm/liter (grams per liter) dry mass equivalent; (d) The light-dark periods average the light to all the algae in the media; (e) The spinning is operated at as high a speed as can be obtained before damage to the algae; (f) The tubes are oriented vertical to minimize bowing and allow for tubes to be as long as possible; (g) The spinning light rods are lit with LEDs that are arranged in a pattern to generate a uniform light on the outside surface of the light rod; (h) The LEDs are mounted on a finned tube where the fins reflect light that would normally be lost to total internal reflection. The LEDs and PCB board are protected from reaction with the thermal control fluid by burial under a glass surfaces using optical epoxy materials; (i) A thermal control fluid is circulated to control the temperature of the LEDs and control the temperature of the growth media; (j) The LEDs are of a wavelength(s) and intensity to enhance the specific growth phase and species of algae or cyanobacteria; (k) The peak light intensity is much higher than would be generated by photo inhabitation in the algae if the algae was not in motion; (l) There are a large number of spinning rods configured close to each other to enhance the light emitting surface area to media volume; (m) The surface of the rotating tube is smooth and particular attention is given to reduce stress in the fluid; and/or (n) The surface is given features or surface finish to change the friction between the spinning rod surface and the fluid.

A rotating head coupled to the rotating light rod that incorporates the power transfer to the rotating environment of the spinning light rod, wherein: (a) The power coupling is by brush and slip ring; and/or (b) The power coupling is by split transformer. Additionally, a rotating head, wherein the motor to spin the tube is mounted coaxially on the tube, wherein the tubes are arranges in a hex pattern (7 spinning rods). Half pumping in toward the central tube and half pumping away.

The photo-bioreactor system can include a rotating head having means to couple electronic digital data from the rotating spinning rod and the stationary part of the system, and wherein: (a) This data includes temperature of the fluid; (b) The data is at buss voltage on the rotating part of the system; (c) The data includes the current through each LED; (d) The data includes diagnostics on the algae mounted in the spinning light tube, such as: (i) Chlorophyll and, by inference, algae density, (ii) Product density, (iii) pH by fluorescence measurement of surface dots, (iv) Nutrients by fluorescence measurement of surface dots, (v) Dissolved Oxygen and dissolved $CO_2$ by fluorescence measurement of surface dots.

The photo-bioreactor system can include seals, materials of construction, and design that allow the photo-bioreactor to be steam sterilized. Additionally, the system includes means for mechanically abrading the photo-bioreactor interior surface including the spinning rods for removal of bio films. Additionally yet, the system includes means for enzymatic removal of bio films.

The photo-bioreactor system can include at least two tanks with connecting channels between the tanks, one near the top and one near the bottom, wherein at the bottom of one tank, air is injected in small bubbles and causes air lifting of the media. Airlifting causes circulation of the algae and enhances release of dissolved oxygen produced by the algae growth process.

The photo-bioreactor system can generate bubbles by the injection of air or other gas into the media and extracting the bubbles from the growth media. These bubbles contain a high quantity of algae growth process residual material.

The photo-bioreactor system can include a design, wherein the bubble stream is extracted through a narrow passage, and wherein it is rinsed into solution and removed from the system. The bubble extraction system can be configured to be steam sterilized.

The photo-bioreactor system can include an aeration system that is integrated with the spinning tubes, wherein the tubes have bearings on the bottom (in the preferred design) to stabilize their rotation, and wherein: (a) These bearings are purged to minimize damaging in the bearing; (b) The bearings are surrounded with gas-emitting surfaces that provide the aeration, provide lift bubble source and bubbles to produce bubbles that extract growth byproducts, some of which are inhibiting to algae growth; (c) These gas-emitting surfaces are made of material that can be used to inject steam during sterilization; (c) The gas-emitting surfaces are sterilized very completely while the chamber is sterilized; and/or (d) The gas emitting surfaces are powdered stainless steel sponge.

The photo-bioreactor system can include a system having a side stream, wherein the media is treated much like a dialysis machine for blood, and wherein: (a) The first media membrane is designed to allow everything but algae to pass through the membrane; (b) The second membrane allows water and nutrients to pass through the second membrane. This stream is treated and returned to the media; (c) The material between the two membranes is enhanced in algae growth byproducts and facilitates removal of these byproducts from the growth media; (d) This side stream is at least partially the harvest stream providing a partial dewatering of the algae.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

The invention claimed is:

1. A photo-bioreactor, comprising:
   a reactor vessel arranged to contain a fluid medium within an exterior reactor wall within which bio-material is grown;
   a plurality of light-emitting rods extending into said reactor vessel, each light-emitting rod comprising an elongate tubular member characterized by a length along a longitudinal axis and a width along an axis normal to said longitudinal axis, and designed with an enclosing wall that encloses one or more light-emitting devices arranged along said longitudinal axis, said enclosing wall being transparent to at least part of the light emitted by said light-emitting devices into said reactor vessel; and
   a drive system coupled to said elongate tubular member, and operatively configured to rotate said light-emitting rods about their respective longitudinal axes within said reactor vessel.

2. The photo-bioreactor of claim 1, further comprising:
   a controller coupled to said drive system, and programmed to actuate said light-emitting rods according to at least one of the following rotational modes:
   intermittently or continuously rotate said light-emitting rods in a first direction about said longitudinal axes at a pre-determined rotation rate, or predetermined sequence of rotation rates, or rotatably oscillate said light-emitting rods about said longitudinal axes at a pre-determined oscillation frequency, and oscillation amplitude.

3. The photo-bioreactor of claim 1, wherein said plurality of light-emitting rods comprises:
a first light-emitting rod extending into said reactor vessel;
a second light-emitting rod extending into said reactor vessel, and spaced apart a proximal distance from said first light-emitting rod; and
a controller coupled to said drive system, and programmed to rotate said first light-emitting rod in a first direction about a longitudinal axis of said first light-emitting rod, and rotate said second-light-emitting rod in a second direction about a longitudinal axis of said second light-emitting rod.

4. The photo-bioreactor of claim 3, wherein said second direction opposing said first direction, and said rotating said first and second light-emitting rods acting to pump fluid medium in said reactor vessel through the spaced apart region between said first and second light-emitting rods.

5. The photo-bioreactor of claim 1, wherein said plurality of light-emitting rods comprises:
a first array of light-emitting rods extending into said reactor vessel arranged according to a first pattern, said first pattern comprising: an inner light-emitting rod centrally located in said first pattern, and
an even number of outer light-emitting rods peripherally located in said first pattern, and arranged about said inner light-emitting rod at azimuthally spaced intervals; and
a controller coupled to said drive system, and programmed to actuate said light-emitting rods in the following manner:
rotate said inner light-emitting rod about a longitudinal axis of said inner light-emitting rod, rotatably oscillate said inner light-emitting said longitudinal axis of said inner light-emitting rod, or maintain said inner light-emitting rod stationary, and
rotate each of said even number of outer light-emitting rods such that adjacent outer light-emitting rods rotate in opposing directions about their respective axes.

6. The photo-bioreactor of claim 5, wherein at least two of said even number of outer light-emitting rods rotate in opposing direction about their respective axes so as to pump said fluid medium either inward towards said inner light-emitting rod, or outward away from said inner light-emitting rod.

7. The photo-bioreactor of claim 5, wherein adjacent outer light-emitting rods of said even number of outer light-emitting rods counter-rotate relative to one another to pump said fluid medium towards said inner light-emitting rod in first azimuthally spaced regions, and pump said fluid medium away from said inner light-emitting rod in second azimuthally spaced regions.

8. The photo-bioreactor of claim 5, wherein said first pattern comprises a hexagonal pattern of outer light-emitting rods.

9. The photo-bioreactor of claim 5, wherein said plurality of light-emitting rods comprises further comprises:
a second array of light-emitting rods extending into said reactor vessel arranged according to a second pattern, said second pattern comprising:
an inner light-emitting rod centrally located in said second pattern, and
an even number of outer light-emitting rods peripherally located in said second pattern, and arranged about said inner light-emitting rod at azimuthally spaced intervals,
wherein said first pattern of light-emitting rods and said second pattern of light-emitting rods share at least one outer lighting-emitting rod.

10. The photo-bioreactor of claim 9, wherein said first and second patterns comprise hexagonal patterns of outer light-emitting rods.

11. The photo-bioreactor of claim 1, further comprising:
at least one sensor mounted on or within at least one of said light-emitting rods; and
a diagnostic system coupled to said at least one sensor, and programmed to collect and monitor data from said at least one sensor, said data including a fluid temperature of said fluid medium, an electrical signal related to rotation of said at least one light-emitting rod, an electrical signal related to operation of said one or more light-emitting devices, bio-material density in said fluid medium, pH, nutrient level in said fluid medium, oxygen content in said fluid medium, carbon dioxide content in said fluid medium.

12. The photo-bioreactor of claim 1, further comprising:
an aeration system coupled to said reactor vessel, and arranged to inject a gas into said fluid medium.

13. The photo-bioreactor of claim 1, further comprising:
a cleaning system coupled to said reactor vessel, and arranged to provide a cleaning fluid into said reactor vessel to clean interior surfaces of said reactor vessel.

14. The photo-bioreactor of claim 5, wherein said first array comprises seven light-emitting rods.

15. A photo-bioreactor, comprising:
a reactor vessel arranged to contain a fluid medium within which bio-material is grown;
at least one light-emitting rod extending into said reactor vessel, said light-emitting rod comprising an elongate tubular member characterized by a length along a longitudinal axis and a width along an axis normal to said longitudinal axis, and designed with an enclosing wall that encloses one or more light-emitting devices arranged along said longitudinal axis, said enclosing wall being transparent to at least part of the light emitted by said one or more light-emitting devices into said reactor vessel; and
a drive system coupled to said elongate tubular member, and operatively configured to rotate said light-emitting rod about said longitudinal axis within reactor vessel;
wherein said at least one light-emitting rod comprises:
a center body that extends through an interior of said elongate tubular member along at least a portion of the length of said elongate tubular member and creates an annular space between an outer surface of said center body and in inner surface of said elongate tubular member, wherein said one or more light-emitting devices are mounted upon said outer surface of said center body; and
at least one fin extending from said outer surface of said elongate member towards said inner surface of said elongate tubular member, said at least one fin being configured to reflect light emitted from said one or more light-emitting devices outward from said elongate tubular member.

16. The photo-bioreactor of claim 15, wherein said one or more light-emitting devices are encapsulated within an optically transparent material on said outer surface of said center body to hermetically seal said one or more light-emitting devices from the environment in said annular space.

17. The photo-bioreactor of claim 16, further comprising:
a temperature control system for controlling a temperature of said one or more light-emitting devices, said temperature control system comprising a fluid circulation system for pumping a heat transfer fluid through said annular space over said one or more light-emitting devices.

* * * * *